United States Patent [19]

Fiddes et al.

[11] Patent Number: 5,604,293

[45] Date of Patent: Feb. 18, 1997

[54] RECOMBINANT HUMAN BASIC FIBROBLAST GROWTH FACTOR

[75] Inventors: John C. Fiddes, Palo Alto; Judith A. Abraham, Sunnyvale, both of Calif.

[73] Assignee: Scios Inc., Mountain View, Calif.

[21] Appl. No.: 221,462

[22] Filed: Apr. 1, 1994

Related U.S. Application Data

[63] Continuation of Ser. No. 860,688, Mar. 30, 1992, abandoned, which is a continuation of Ser. No. 50,706, May 15, 1987, abandoned, which is a continuation-in-part of Ser. No. 869,382, May 30, 1986, abandoned, and Ser. No. 809,163, Dec. 16, 1985, Pat. No. 5,439,818, and Ser. No. 775,521, Sep. 12, 1985, abandoned.

[51] Int. Cl.$^6$ .................................................. C07K 14/50
[52] U.S. Cl. ...................................... 530/399; 930/10
[58] Field of Search .............................. 530/399, 350; 514/12; 930/10

[56] References Cited

U.S. PATENT DOCUMENTS

| | | | |
|---|---|---|---|
| 4,956,455 | 9/1990 | Esch et al. | 530/399 |
| 5,155,214 | 10/1992 | Baird et al. | 530/399 |

OTHER PUBLICATIONS

Iwane et al, "Expression of cDNA Encoding Human Basic Fibroblast Growth Factor in *E. coli*," *Biochem. Biophys. Res. Comm.*, 146:470–477 (1987).

Thompson et al, "Cloning, Recombinant Expression, and Characterization of Basic Fibroblast Growth Factor," *Methods Enzymol.*, 198:96–116 (1991).

Fox et al, "Production, Biological Activity, and Structure of Recombinant Basic Fibroblast Growth Factor and an Analog . . . ," *J. Biol. Chem.*, 263:18452–18458 (1988).

Thompson et al, "The Disulfide Structure of Bovine Pituitary Basic Fibroblast Growth Factor," *J. Biol. Chem.*, 267:2269–2273 (1992).

Conn et al, "The Isolation and Purification of Two Anionic Endothelial Cell Growth Factors from Human Brain," *Biochem. Biophys. Res. Comm.*, 124:262–268 (1984).

Bohlen et al., "Acidic Fibroblast Growth Factor (FGF) from Bovine Brain: Amino-Terminal Sequence and Comparison with Basic FGF," *EMBO J.*, 4:1951–1956 (1985).

Abraham et al., *J. Cell. Biochem. Supplement*, vol. 0, No. 11, p. 50, Abst No. 191, 1987.

Guillermo Gimenez-Gallego et al., *Biochem. Biophy. Res. Communications*, vol. 135, No. 2, 541–548, 1986.

Esch et al. Proc. Natl. Acad. Sci. USA, vol. 82, 6507–6511, 1985.

Bohlen et al., Proc. Natl. Acad. Sci., USA, vol. 81, 5364–5368, 1984.

Gospodarowicz et al., *Biochem. Biophy. Res. Communications*, vol. 128, No. 2, 554–562, 1985.

*Primary Examiner*—John Ulm
*Assistant Examiner*—Christine Saoud
*Attorney, Agent, or Firm*—Burns, Doane, Swecker & Mathis, L.L.P.

[57] ABSTRACT

The DNA sequences encoding human and bovine acidic and basic fibroblast growth factors (FGF) can be recombinantly expressed to obtain practical amounts of proteins useful in effecting wound healing and related tissue repair.

4 Claims, 18 Drawing Sheets

```
                                                            AGC
TGC TGA GCC ATG GCT GAA GGA GAA ACC ACG ACC TTC ACG GCC CTG ACT GAG AAG
        (Met Ala Glu Gly Glu Thr Thr Thr Phe Thr Ala Leu Thr Glu Lys)
         -15                                                         -1

TTT AAC CTG CCT CTA GGC AAT TAC AAG AAG CCC AAG CTC CTC TAC TGC AGC AAC
Phe Asn Leu Pro Leu Gly Asn Tyr Lys Lys Pro Lys Leu Leu Tyr Cys Ser Asn
 1                                        10

GGG GGC TAC TTC CTG AGA ATC CTC CCA GAT GGC ACA GTG GAT GGG ACG AAG GAC
Gly Gly Tyr Phe Leu Arg Ile Leu Pro Asp Gly Thr Val Asp Gly Thr Lys Asp
         20                                30

AGG AGC GAC CAG CAC A GTAAGCACCCATCTCTCACATTTCTGGTATCTTCCTTACTCAGGGACAGGA
Arg Ser Asp Gln His
         40

GAAGGGAGAATAGGGAGAATAGCTAAGGGCT
```

FIG. 1a

```
                                                                    T
GCT GAG GCC ATG GCT GAA GGG GAA ATC ACC ACC TTC ACA GCC CTG ACC GAG AAG
            (Met Ala Glu Gly Glu Ile Thr Thr Phe Thr Ala Leu Thr Glu Lys)
             -15                                                      -1

TTT AAT CTG CCT CCA GGG AAT TAC AAG AAG CCC AAA CTC CTC TAC TGT AGC AAC
Phe Asn Leu Pro Pro Gly Asn Tyr Lys Lys Pro Lys Leu Leu Tyr Cys Ser Asn
 1                               10

GGG GGC CAC TTC CTG AGG ATC CTT CCG GAT GGC ACA GTG GAT GGG ACA AGG GAC
Gly Gly His Phe Leu Arg Ile Leu Pro Asp Gly Thr Val Asp Gly Thr Arg Asp
     20                                  30

AGG AGC GAC CAG CAC A GTAAGCCCATCTCTATGGC
Arg Ser Asp Gln His
             40
```

FIG. 2a

```
TGT TTA TTT ACT TTT GCT CGT GTT ATT TTT ATT CCA GTT CAG CTG CAG CTC AGT
                                                 al  Gln Leu Gln Leu Ser
                                                 42

GCG GAA AGC GTG GGG GAG GTG TAT ATA AAG AGT ACC GAG ACT GGC CAG TAC TTG
Ala Glu Ser Val Gly Glu Val Tyr Ile Lys Ser Thr Glu Thr Gly Gln Tyr Leu
         50                                  60

GCC ATG GAC ACC GAC GGG CTT TTA TAC GGC TCA GTA AGT ATG AAG TAG ACA TGC
Ala MET Asp Thr Asp Gly Leu Leu Tyr Gly Ser
             70

TTC CAG ACG TTG GCC TTG GTT
```

```
TGT GAA ACT ACT CAC TGA TTG TCC TAC TCT CTT GTG GTT TTA TCT TTT TAG CAG
                                                                        Gln
                                                                         77

ACA CCA AAT GAG GAA TGT TTG TTC CTG GAA AGG CTG GAG GAG AAC CAT TAC AAC
Thr Pro Asn Glu Glu Cys Leu Phe Leu Glu Arg Leu Glu Glu Asn His Tyr Asn
                                                        90

ACC TAT ATA TCC AAG AAG CAT GCA GAG AAG AAT TGG TTT GTT GGC CTC AAG AAG
Thr Tyr Ile Ser Lys Lys His Ala Glu Lys Asn Trp Phe Val Gly Leu Lys Lys
            100                                     110

AAT GG...
Asn Gly...
```

FIG. 2d

```
                                                EcoRI                                                                                     -1
                                                GAATTCGGGAACGCGCCACAAGCAGCAGCTGCTGAGCC
                                                                                                                                         120
  1
ATGGCTGAAGGGGAAATCACCACCTTCACAGCCCTGACCGAGAAGTTTAATCTGCCTCCAGGGAATTACAAGAAGCCCAAGCTCCTCTACTGTAGCAACGGGGGCCACTTCCTGAGGATC
 M  A  E  G  E  I  T  T  F  T  A  L  T  E  K  F  N  L  P  P  G  N  Y  K  K  P  K  L  L  Y  C  S  N  G  G  H  F  L  R  I
-15            -10                -5                -1 +1              5                        10
                                                           PstI                                                                          240

CTTCCGGATGGCACAGTGGACAAGGAGACAGGAGCGACCAGCACATTCAGCTGCAGCTCAGTGCGGAAAGCGTGGGGAGGTGTATATAAAGAGTACCGAGACTGGCCAGTACTTG
 L  P  D  G  T  V  D  K  E  T  G  A  T  S  T  F  S  C  S  S  V  R  K  A  W  G  G  V  Y  I  K  S  T  E  T  G  Q  Y  L
                                                                                                        SphI                             360

GCCATGGACACCGACGGGCTTTTATACGGCTCACAGAGAACACAAATGAGGAGCTGCAAACGCGGTCCTCGGACTCACTATGGCCAGAAAGCAATCTTGTTTCTCCCCCTGCAGTCTCTTC
 A  M  D  T  D  G  L  L  Y  G  S  Q  T  P  N  E  E  C  L  F  L  E  R  L  E  E  N  H  Y  N  T  Y  I  S  K  K  H  A  E  K
                                                                                                                                         480

AATTGGTTTGTTGGCCTCAAGAAGAATGGGAGCTGCAAACGCGGTCCTCGGACTCACTATGGCCAGAAAGCAATCTTGTTTCTCCCCCTGCAGTCTCTTCTGATTAAAGAGATCTGTTC
 N  W  F  V  G  L  K  K  N  G  S  C  K  R  G  P  R  T  H  Y  G  Q  K  A  I  L  F  L  P  L  P  Y  S  S  D  *
                                                                                                                                         600

TGGTGTTGACCACTCCAGAGAAGTTTCGAGGGGTCCTCACCTGGTTGACCCCAAAAATGTCCCTGACCATTGGCTGCTAACCCCCAGCCCCAGAGAGCCTGAATTTGTAAGCAACTT
```

```
                        ATG GCC TCC GGG AGC ATC ACC ACG CTG
                       (Met Ala Gla Gly Ser Ile Thr Thr Leu)
                        -9                                -1

CCA GCC CTG CCG GAG GAC GGC GGC AGC GGC GCT TTC CCG CCG GGC CAC
Pro Ala Leu Pro Glu Asp Gly Gly Ser Gly Ala Phe Pro Pro Gly His
 1                                10

TTC AAG GAC CCC AAG CGG CTG TAC TGC AAG AAC GGG GGC TTC TTC CTG
Phe Lys Asp Pro Lys Arg Leu Tyr Cys Lys Asn Gly Gly Phe Phe Leu
             20                                         30

CGC ATC CAC CCC GAC GGC CGA GTG GAC GGG GTC CGC GAG AAG AGC GAC
Arg Ile His Pro Asp Gly Arg Val Asp Gly Val Arg Glu Lys Ser Asp
                         40

CCA CAC ATC AAA CTA CAA CTT CAA GCA GAA GAG AGA GGG GTT GTG TCT
Pro His Ile Lys Leu Gln Leu Gln Ala Glu Glu Arg Gly Val Val Ser
     50                                 60

ATC AAA GGA GTG TGT GCA AAC CGT TAC CTT GCT ATG AAA GAA GAT GGA
Ile Lys Gly Val Cys Ala Asn Arg Tyr Leu Ala Met Lys Glu Asp Gly
                 70                                         80

AGA TTA CTA GCT TCT AAA TGT GTT ACA GAC GAG TGT TTC TTT TTT GAA
Arg Leu Leu Ala Ser Lys Cys Val Thr Asp Glu Cys Phe Phe Phe Glu
                             90

CGA TTG GAG TCT AAT AAC TAC AAT ACT TAC CGG TCA AGG AAA TAC TCC
Arg Leu Glu Ser Asn Asn Tyr Asn Thr Tyr Arg Ser Arg Lys Tyr Ser
                 100                                        110

AGT TGG TAT GTG GCA CTG AAA CGA ACT GGG CAG TAT AAA CTT GGA CCC
Ser Trp Tyr Val Ala Leu Lys Arg Thr Gly Gln Tyr Lys Leu Gly Pro
                             120

AAA ACA GGA CCT GGG CAG AAA GCT ATA CTT TTT CTT CCA ATG TCT GCT
Lys Thr Gly Pro Gly Gln Lys Ala Ile Leu Phe Leu Pro Met Ser Ala
     130                                    140

AAG AGC TGA TCT TAA
Lys Ser Ter     Ter
        146
```

FIG. 3

```
                              ATG GCA GCC GGG AGC ATC ACC ACG CTG
                             (Met Ala Ala Gly Ser Ile Thr Thr Leu)
                              -9                                -1

CCC GCC TTG CCC GAG GAT GGC GGC AGC GGC GCC TTC CCG CCC GGC CAC
Pro Ala Leu Pro Glu Asp Gly Gly Ser Gly Ala Phe Pro Pro Gly His
 1                                    10

TTC AAG GAC CCC AAG CGG CTG TAC TGC AAA AAC GGG GGC TTC TTC CTG
Phe Lys Asp Pro Lys Arg Leu Tyr Cys Lys Asn Gly Gly Phe Phe Leu
          20                                          30

CGC ATC CAC CCC GAC GGC CGA GTT GAC GGG GTC CGG GAG AAG AGC GAC
Arg Ile His Pro Asp Gly Arg Val Asp Gly Val Arg Glu Lys Ser Asp
                         40

CCT CAC ATC AAG CTA CAA CTT CAA GCA GAA GAG AGA GGA GTT GTG TCT
Pro His Ile Lys Leu Gln Leu Gln Ala Glu Glu Arg Gly Val Val Ser
         50                                  60

ATC AAA GGA GTG TGT GCT AAC CGT TAC CTG GCT ATG AAG GAA GAT GGA
Ile Lys Gly Val Cys Ala Asn Arg Tyr Leu Ala Met Lys Glu Asp Gly
                     70                                       80

AGA TTA CTG GCT TCT AAA TGT GTT ACG GAT GAG TGT TTC TTT TTT GAA
Arg Leu Leu Ala Ser Lys Cys Val Thr Asp Glu Cys Phe Phe Phe Glu
                                 90

CGA TTG GAA TCT AAT AAC TAC AAT ACT TAC CGG TCA AGG AAA TAC ACC
Arg Leu Glu Ser Asn Asn Tyr Asn Thr Tyr Arg Ser Arg Lys Tyr Thr
             100                                      110

AGT TGG TAT GTG GCA TTG AAA CGA ACT GGG CAG TAT AAA CTT GGA TCC
Ser Trp Tyr Val Ala Leu Lys Arg Thr Gly Gln Tyr Lys Leu Gly Ser
                             120

AAA ACA GGA CCT GGG CAG AAA GCT ATA CTT TTT CTT CCA ATG TCT GCT
Lys Thr Gly Pro Gly Gln Lys Ala Ile Leu Phe Leu Pro Met Ser Ala
     130                                         140

AAG AGC TGA TTT TAA
Lys Ser Ter     Ter
     146
```

FIG. 4

```
                1                               10
     phe asn leu pro leu gly asn tyr lys lys pro lys leu leu tyr cys ser          amino acid sequence 5'   TTT AAT CTX CCX CTX GGX AAT TAT AAA AAA CCX AAA CTX CTX TAT TGT TCX    3'    coding sequence
       C   C           TTA   C     G   G         G               C   C
                       TTG                                       TTA AGT
                                                                 TTG   C 3'   AAG TTG GAC GGG GAC GAC CGG TTG ATG TTC TTC GGG TTC GAC GAC ATG ACG          probe 891
                                     TTA ATA TTT TTT GGX TT        5'             probes 853-856
                        3'           TTG     C   C                                
                                         ATG 20                           30
     asn gly cys tyr phe leu arg ile leu pro asp gly thr val asp gly thr 5'   AAT GGX TGT TAT TTT CTX CGX ATT CTX CCX GAT GGX ACX GTX GAT GGX ACX    3'
       C     C   C   C         A     C         C             C
                   TTA AGA     TTG
                   TTG 3'   TTA CCG ACG ATG AAG GAC GCG TAG GAC GGA CTA CCG TGA CAC CTA CCG TGG    5'    probes 889/890
                             TCT

FIG. 5
```

```
         AGCTGCTGAGCCATGGCTGAAGGAGAAACCACGACCTTCACGGCCCTGACTGAGAAG
         AluI

TTT AAC CTG CCT CTA GGC AAT TAC AAG AAG CCC AAG CTC CTC TAC TGC AGC AAC
Phe Asn Leu Pro Leu Gly Asn Tyr Lys Lys Pro Lys Leu Leu Tyr Cys Ser Asn
 1                              10

GGG GGC TAC TTC CTG AGA ATC CTC CCA GAT GGC ACA GTG GAT GGG ACG AAG GAC
Gly Gly Tyr Phe Leu Arg Ile Leu Pro Asp Gly Thr Val Asp Gly Thr Lys Asp
     20                             30

AGG AGC GAC CAG CAC A GTAAGCACCCATCTCACATTTCTGGTATCTTCCTTACTCAGGGACAGGA
Arg Ser Asp Gln His
             40

GAAGGGAGAATAGGGAGAATAGCTAAGGGCT
                    AluI
```

FIG. 7

NcoI

```
         10         20         30         40         50
CCATGGCTGA AGGGGAAATC ACCACCTTCA CAGCCCTGAC CGAGAAGTTT
GGTACCGACT TCCCCTTTAG TGGTGGAAGT GTCGGGACTG GCTCTTCAAA 60         70         80         90        100
AATCTGCCTC CAGGGAATTA CAAGAAGCCC AAACTCCTCT ACTGTAGCAA
TTAGACGGAG GTCCCTTAAT GTTCTTCGGG TTTGAGGAGA TGACATCGTT
```

BamHI

```
        110        120        130    ①   140        150
CGGGGGCCAC TTCCTGAGGA TCCTTCCGGA TGGCACAGTG GATGGGACAA
GCCCCCGGTG AAGGACTCCT AGGAAGGCCT ACCGTGTCAC CTACCCTGTT
                                     ⑪

160        170    ②   180        190        200
GGGACAGGAG CGACCAGCAC ATTCAGCTGC AGCTCAGTGC GGAAAGCGTG
CCCTGTCCTC GCTGGTCGTG TAAGTCGACG TCGAGTCACG CCTTTCGCAC
                      ⑫

210 ③     220        230        240  ④  *  250
GGGGAGGTGT ATATAAAGAG TACCGAGACT GGCCAGTACT TGGCTATGGA
CCCCTCCACA TATATTTCTC ATGGCTCTGA CCGGTCATGA ACCGATACCT
              ⑬                              ⑭

260        270        280  ⑤   290        300
CACCGACGGG CTTTTATACG GCTCACAGAC ACCAAATGAG GAATGTTTGT
GTGGCTGCCC GAAAATATGC CGAGTGTCTG TGGTTTACTC CTTACAAACA
                                  ⑮

310        320  ⑥   330        340   ⑦  350
TCCTGGAAAG GCTGGAGGAG AACCATTACA ACACCTATAT ATCCAAGAAG
AGGACCTTTC CGACCTCCTC TTGGTAATGT TGTGGATATA TAGGTTCTTC
                           ⑯                  ⑰

360        370        380   ⑧  390        400
CATGCAGAGA AGAATTGGTT TGTTGGCCTC AAGAAGAATG GGAGCTGCAA
GTACGTCTCT TCTTAACCAA ACAACCGGAG TTCTTCTTAC CCTCGACGTT
                                    ⑱

410        420  ⑨   430        440        450
ACGCGGTCCT CGGACTCACT ATGGCCAGAA AGCAATCTTG TTTCTCCCCC
TGCGCCAGGA GCCTGAGTGA TACCGGTCTT TCGTTAGAAC AAAGAGGGGG
                                              EcoRI        ⑲
        460   ⑩   470        HindIII 480
TGCCAGTCTC TTCTGATTGA AGCTTGAATT C
ACGGTCAGAG AAGACTAACT TCGAACTTAA G
              ⑳
```

*NcoI site

FIG. 9

```
acidic                  9
FGF                     lys lys pro lys leu leu tyr cys ser asn gly gly tyr phe leu arg ile leu pro  27
known
coding      5'  AAG AAG CCC AAG CTC CTC TAC TGC AGC AAC GGG GGC TAC TTC CTG AGA ATC CTC CCA  3'
sequence basic                   18                                                              36
FGF                     lys asp pro lys arg leu tyr cys lys asn gly gly phe phe leu arg ile his pro
potential
coding      5'  AAG GAC CCC AAG CGC CTC TAC TGC AAG AAC GGG GGC TTC TTC CTG AGA ATC CAC CCA  3'
sequence probe       3'  TTC CTG GGG TTC GCG GAG ATG ACG TTC TTG CCC CCG AAG A   5'
1098 probe               3'  G ATG ACG TTC TTG CCC CCG AAG AAG GAC TCT TAG GTG GGT  5'
1097
```

FIG. 10

```
                                Ia
                ATGGCCGCCG GGAGCATCAC CACGCTGCCA GCCCTGCCGG
                TACCGGCGGC CCTCGTAGTG GTGCGACGGT CGGGACGGCC
             III           IIa                  Va
①  AGGACGGCGG CAGCGGCGCT TTCCCGCCGG GCCACTTCAA GGACCCCAAG
   TCCTGCCGCC GTCGCCGCGA AAGGGCGGCC CGGTGAAGTT CCTGGGGTTC
            IV                      VIa
                                                      HhaI
   CGGCTGTACT GCAAGAACGG GGGCTTCTTC CTGCG
   GCCGACATGA CGTTCTTGCC CCCGAAGAAG GAC
              VIII

Ib
                GCTGCCGCCG GGAGCATCAC CACGCTGCCA GCCCTGCCGG
                CGACGGCGGC CCTCGTAGTG GTGCGACGGT CGGGACGGCC
             III           IIb                  Va
   AGGACGGCGG CAGCGGCGCT TTCCCGCCGG GCCACTTCAA GGACCCCAAG
   TCCTGCCGCC GTCGCCGCGA AAGGGCGGCC CGGTGAAGTT CCTGGGGTTC
②           IV                      VIa
                                                      HhaI
   CGGCTGTACT GCAAGAACGG GGGCTTCTTC CTGCGC
   GCCGACATGA CGTTCTTGCC CCCGAAGAAG GACG
              VIII

③                                                                         HhaI
           Vc                                VII
  TTCCCGCCGG GCCACTTCAA GGACCCCAAGCGGCTGTACT GCAAGAACGG GGGCTTCTTC CTGCG
  AAGGGCGGCC CGGTGAAGTT CCTGGGGTTCGCCGACATGA CGTTCTTGCC CCCGAAGAAG GAC
           Vic                                VIII

HhaI
④         Vd                              VII
      CACTTCAA GGACCCCAAG CGGCTGTACT GCAAGAACGG GGGCTTCTTC CTGCG
      GTGAAGTT CCTGGGGTTC GCCGACATGA CGTTCTTGCC CCCGAAGAAG GAC
           Vid                            VIII
```

FIG. 13

```
                    ↓
hGH  ...Q E G S A F P T I...
              |      ?
              | ↓-9         ↓        -1+1         10            ?    20
A    ...Q E G S A M A A G S I T T L P A L E P D G G S G A F P P G H F K D P...
              |    ↓-8      ↓?        -1+1        10            ?    20
B    ...Q E G S A A A G S I T T L I A L P E D G G S G A F P P G H F K D P...
              ↓
              12    ?          20
C    ...Q E G S A F P P G H F K D P K
              ↓
              16       20
D    ...Q E G S A H F K D P K...
              |
              | -9         -1+1        10                       20
FGF           M A A G S I T T L I A L P E D G G S G A F P P G H F K D P...
              |
    ←—hGH     |basic hFGF —→
```

FIG. 14

```
                    ↓
hGH  ...Q E G S A F P T I...
              |                    ?           ?
              | ↓-14    -10        ↓-1+1       ↓         10
E    ...Q E G S A A A E G E I T T F T A L T E K F N L P P G N Y K K P K L L Y...
              | ↓
              | +1       ?         10
F    ...Q E G S A A F N L P P G N Y K K P K L L Y...
              |
              |6↓        10
G    ...Q E G S A G N Y K K P K L L Y...
              |
              | -15     -10        -1+1         10
FGF           M A E G E I T T F T A L T E K F N L P P G N Y K K P K L L Y...
              |
    ←—hGH     |acidic hFGF —→
```

FIG. 15

```
            IX                                                      XI
GCTGCTGA AGGGGAAATC ACCACCTTCA CAGCCCTGAC CGAGAAGTTT AATCTGCCTC CA
CGACGACT TCCCCTTTAG TGGTGGAAGT GTCGGGACTG GCTCTTCAAA TTAGACGGAG GT
            X                                                      XII
                              XIII
                    GCTTTTAATCTGCCTC CA
                    CGAAAATTAGACGGAG GT
                              XIV
```

FIG. 16

RECOMBINANT HUMAN BASIC FIBROBLAST GROWTH FACTOR

This application is a continuation of U.S. Ser. No. 07/860,688, filed Mar. 30, 1992, now abandoned; which is a continuation of U.S. Ser. No. 07/050,706, filed May 15, 1987, now abandoned; which is a continuation-in-part of U.S. Ser. No. 06/869,382, filed May 30, 1986, now abandoned; and a continuation-in-part of U.S. Ser. No. 06/809,163, filed Dec. 16, 1985, now U.S. Pat. No. 5,439,818; and a continuation-in-part of U.S. Ser. No. 06/775,521, filed Sep. 12, 1985, now abandoned.

TECHNICAL FIELD

The invention relates to recombinant production of growth factors important for constructing vascular systems in healing tissues. In particular, the genes encoding bovine and human basic and acidic fibroblast growth factors (FGF) are cloned and expressed.

BACKGROUND ART

The process of healing when tissue is subjected to trauma, such as wounding or burns, is an extremely complex one, but it is known to be mediated by a number of protein factors. These factors are essential to the growth and differentiation of the cells which serve to replace the tissue destroyed. A number of candidate factors have been identified on the basis of the ability of extracts from various tissues, such as brain, pituitary, and hypothalamus, to stimulate the mitosis of cultured cell lines. Numerous shorthand names have been applied to the active factors in these extracts, including platelet-derived growth factor (PDGF), macrophage-derived growth factor (MDGF), epidermal growth factor (EGF), tumor anglogenesis factor (TAF), endothelial cell growth factor (ECGF), fibroblast growth factor (FGF), hypothalamus-derived growth factor (HDGF), retina-derived growth factor (RDGF), and heparin-binding growth factor (HGF). (See, for example, Hunt, T. K., *J Trauma* (1984) 24:S39-S49: Lobb, R. R., et al, *Biochemistry* (1984) 23:6295–6299).

Folkman, J., et al, *Science* (1983) 221:719–725, reported that one of the processes involved in wound, healing, the formation of blood vessels, is profoundly affected in tumors by heparin. From this and other studies, it is clear that heparin specifically binds to protein(s) associated with a number of these growth factor activities, and therefore heparin has been used as a purification tool. It has been shown that the affinity of growth factors for heparin is independent of overall ionic charge, since both positively and negatively charged factors are bound (Maciag, T., et al, *Science* (1984) 225:932–935: Shing, Y., et al, *Science* (1984) 223:1296–1299; Klagsbrun. M., et al, *Proc Natl Acad Sci* (USA) (1985) 82:805–809). The capacity to bind or not to bind to heparin is one measure of differentiation between the activities in the various extracts. For example, EGF and PDGF do not bind strongly to heparin; in fact, EGF does not bind to heparin at all. The other factors above do show strong heparin binding. However, it is believed that acidic brain FGF, ECGF, RDGF, and HGF-α are in fact the same factor. Similarly, it is also believed that pituitary FGF, cationic brain FGF, TAF, and HGF-β are the same protein. (Lobb, R. R., et al (supra)). A summary and comparison of thirteen endothelial growth factors which have been purified using heparin affinity is found in Lobb; R., et al, *J Biol Chem* (1986) 261:1924–1928.

Using heparin affinity chromatography, basic fibroblast growth factors exhibiting a potent mitogenic activity for capillary endothelium have been isolated from rat chondrosarcoma (Shing, Y., et al, supra) and from bovine cartilage (Sullivan, R., et al, *J Biol Chem* (1985) 260:2399–2403). Thomas, K. A, et al, *Proc Natl Acad Sci* (USA) (1984) 81:357–361, U.S. Pat. No. 4,444,760, purified two heterogeneous forms of an acidic bovine brain fibroblast growth factor having molecular weights of 16,600 and 16,800 daltons. Gospodarowicz and collaborators showed the presence in both bovine brains and pituitaries of basic fibroblast growth factor activities and purified these proteins using heparin-affinity chromatography in combination with other purification techniques (Bohlen, P., et al, *Proc Natl Acad Sci* (USA) (1984) 81:5364–5368; Gospodarowicz, D., et al (ibid) 6963–6967). These factors also have molecular weights of approximately 16 kd, as does a similar factor isolated from human placenta (Gospodarowicz, D., et al, *Biochem Biophys Res Comm* (1985) 128:554–562).

The complete sequence for basic FGF derived from bovine pituitary has been determined (Esch, F., et al, *Proc Natl Acad Sci* (USA) (1985) 82: 6507–6511). Homogeneous preparations were obtained and showed potent mitogenic activity in in vitro assays with endothelial cells (basic FGF has an $ED_{50}$ of 60 pg/ml).

Acidic FGF has an $ED_{50}$ of about 6,000 pg/ml. An N-terminal sequence for acidic FGF derived from bovine brain tissue was determined by Bohlen, P., et al, *EMBO J* (1985) 4:1951–1956. Gimenez-Gallego, G, et al, determined the N-terminal sequences for both acidic and basic FGF prepared from human brain, and compared them to the bovine sequences (*Biochem Biophys Res Comm* (1986) 135:541–548). Their results are consistent with those disclosed herein. Also, the complete amino acid sequence of bovine brain-derived acidic FGF was determined from the isolated protein (Gimenez-Gallego, G, et al, *Science* (1985) 230:1385–1388; Esch, F, et al, *Biochem Biophys Res Comm* (1985) 133:554–562). These two determinations are in agreement with the exception of a single amino acid. Subsequent to much of the work herein, the complete amino acid sequence of human acidic FGF was deduced from the gene (Jaye, M., et al, in press).

The FGF proteins described above and other growth factors are clearly effective in promoting the healing of tissue subjected to trauma (see, e.g., Sporn, M. B., et al, *Science* (1983) 219:1329–1331; Davidson, J. M., et al, *J.C.B.* (1985) 100:1219–1227; Thomas, K. A., et al, *Proc Natl Acad Sci* (USA) (1985) 82:6409–6413). Davidson, et al, (supra) specifically discloses the efficacy of FGF in wound healing. The basic FGF native proteins have been alleged to be useful in treatment of myocardial infarction (Svet-Moldavsky, G. J., et al, *Lancet* (Apr. 23, 1977) 913; U.S. Pat. Nos. 4,296,100 and 4,378,347). In addition, human basic FGF has been found to increase neuronal survival and neurite extension in fetal rat hippocampal neurons (Walicke, P., et al, *Proc Natl Acad Sci* (USA) (1986) 83:3012–3016), suggesting that this factor may also be useful in the treatment of degenerative neurological disorders, such as Alzheimer's disease and Parkinson's disease.

It would, therefore, be desirable to insure the availability of these FGF proteins in large quantities and in a form free from any toxic or infectious impurities. The human form of the protein is preferred, and perhaps required, for therapeutic use. Clearly practical availability cannot be achieved from natural human sources, as obtaining a pure preparation involves an approximately 35,000-fold purification. Even if human cadavers were otherwise a practical source, complete purification would be crucial due to the possibility of transmitting AIDS, hepatitis, or other disease. The recent experience with Creutzfeld-Jacob Syndrome (Powell-Jackson et al, *Lancet* (1985) ii:244–246) precludes the use of human pituitaries as a source. Therefore, recombinant techniques are particularly suitable to apply to the production of these proteins. The invention herein provides the means whereby acidic and basic FGF can be obtained in practical quantities and in pure, uncontaminated form.

DISCLOSURE OF THE INVENTION

The invention provides the tools for synthesis and manipulation of fibroblast growth factors useful in effecting accelerated healing of wounds, bone fractures, burn tissue, damaged myocardial tissue, degenerated neurological tissue, or other trauma. Cloning and expression of the genes encoding these factors are provided by the methods and materials of the invention.

In one aspect, the invention relates to recombinant DNA sequences encoding bovine and human acidic and basic FGF (acidic bFGF, acidic hFGF, basic bFGF, and basic hFGF). In particular, these include the human or bovine genomic sequences. In other aspects, the invention relates to recombinant vectors bearing these DNA sequences, to host cells transformed with such vectors and harboring these DNA sequences, and to the recombinant proteins produced by these transformed cells. In other aspects, the invention relates to methods of producing these fibroblast growth factors using recombinant techniques.

BRIEF DESCRIPTION OF THE DRAWINGS

FIGS. 1A–1B shows the nucleotide and amino acid sequence for acidic bovine FGF. FIG. 1A shows the partial sequence for the acidic bovine FGF and FIG. 1B shows the complete amino acid sequence of this protein.

FIGS. 2A–2D shows the nucleotide and amino acid sequence of human acidic FGF. FIGS. 2A, 2B, and 2C show the nucleotide sequence and deduced amino acid sequence corresponding to the three exons of the human acidic FGF gene contained in λ phage λHAG-9.1, λHG-3, λHAG-3, respectively. FIG. 2D shows the complete amino acid sequence and cDNA sequence encoding human acidic FGF as disclosed by Jaye et al.

FIG. 3 shows the nucleotide sequence of the region of basic bovine FGF encoding amino acids -9 to 146.

FIG. 4 shows the nucleotide sequence of the region of basic human FGF encoding amino acids -9 to 146.

FIG. 5 shows the oligonucleotide probes 889/890, 891 and 853–856 designed from the acidic bFGF N-terminal sequence.

FIG. 7 shows the DNA sequence of the bovine acidic FGF genomic probe 250/AluI.

FIG. 9 shows the partially synthetic gene for acidic hFGF, "Syn-acidic hFGF".

FIG. 10 shows basic FGF probes 1097/1098.

FIG. 13 shows the synthetic oligonucleotides used to construct basic hFGF for fusions to hGH signal sequence.

FIG. 14 shows the amino acid sequence at the hGH/FGF fusion junctions for several basic hFGF recombinant proteins.

FIG. 15 shows the amino acid sequence at the hGH/FGF fusion junctions for several acidic hFGF recombinant proteins.

FIG. 16 shows DNA sequences used to encode portions of certain of the proteins of FIG. 15.

MODES OF CARRYING OUT THE INVENTION

A. The Fibroblast Growth Factors

Figure 1B:
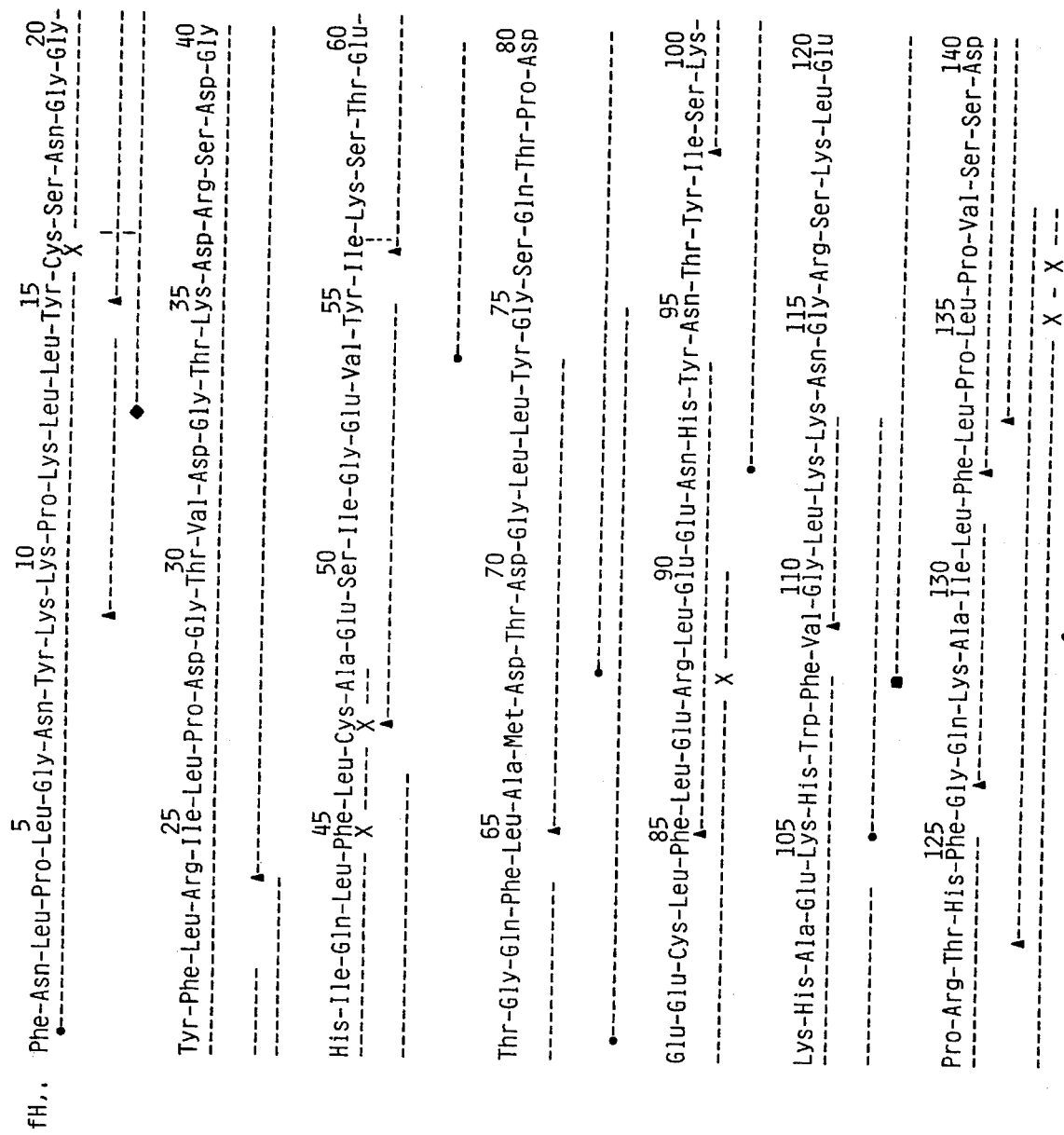

Two different bovine (and analogous human) fibroblast growth factors have been purified to homogeneity by others and partially or completely sequenced. Both factors are capable of mitogenic activity in in vitro assays using cultured cells, such as bovine brain and adrenal cortex-derived capillary endothelial cells, human umbilical vein endothelial cells, bovine adrenal cortex cells, granulosa cells, and vascular smooth muscle cells. In vitro assays employing these cell cultures have been described by Gospodarowicz, D., et al, *J Cell Physiol* (1985) 122:323–332; and Gospodarowicz, D., et al, *J Cell Biol* (1983) 97:1677–1685. More recently, alternative in vitro assays have been described by Esch et al, *Proc Natl Acad Sci* (USA) (1985) 82:6507–6511; and by Gospodarowicz, D., et al, *J Cell Physiol* (1986) 127: 121–136. Purified basic bFGF has been shown to be angiogenic in vivo in a chicken chorioallantoic membrane assay. (Gospodarowicz, D. in *Hormonal Proteins and Peptides* XII:205–230 (Academic Press). Purified acidic bFGF has been shown to be angiogenic in vivo in the same assay (Thomas, K. A., et al, *Proc Natl Acad Sci* (supra)).

Bovine pituitary basic FGF has been completely sequenced and is shown in FIG. 3; the human sequence determined herein from genomic and cDNA is shown in FIG. 4. The primary sequences contain 146 amino acids, beginning with the proline residues numbered "1" in the figures, and are in agreement with the sequence reported for the N-terminus of the native bovine-protein by Giminez-Gallego et al, *Biochem Biophys Res Comm* (supra), and with the sequence reported for the entire native protein by Esch, *Proc Natl Acad Sci* (supra). A higher molecular weight human basic FGF has been reported from the human hepatoma cell line, SK-Hep-1, by Sullivan, R. J., et al, *J Cell Biol* (1985) 101:108a; and by Klagsbrun, M., et al, *Proc Natl Acad Sci* (USA) (1986) 83:2448–2452. Translation of the upstream sequences of FIGS. 3 and 4 back to an ATG start codon in both human and bovine DNA shows that it is likely that an additional form of each protein containing the amino acids upstream of the proline shown as residue 1 in FIGS. 3 and 4 is also produced. There are 9 upstream codons in the DNAs, including the ATG. It is reasonably certain that the methionine encoded by the ATG will be processed when the gene is expressed in eucaryotic systems. Such processing may or may not occur when the gene is expressed recombinantly in bacterial systems. Thus, the long form of the protein contains an additional eight amino acid pro-sequence, or a total of 154 amino acids. It has also been shown that this extended FGF as isolated from SK-HEP-1 cells is blocked at the N-terminus (Klagsbrun, M., et al, (supra)).

Proteins having FGF activity in the above-mentioned in vitro assays and sharing a similar putative N-terminal sequence with the bovine pituitary basic FGF shown in FIG. 3 (the 146 amino acid form) have also been isolated from bovine brain, adrenal gland, corpus luteum, retina, kidney, and from human placenta. The native protein obtained from certain of these tissues is heterogeneous—a second form missing the putative fifteen N-terminal amino acids retains activity. (Gospodarowicz, D., *Meth Enz* (1986) in press.) It is considered, therefore, that bovine and human basic FGFs exist in three forms—those indicated as mature forms in FIGS. 3 and 4, longer forms containing eight additional amino acids at the N-terminus, and shorter forms lacking fifteen amino acids of the putative mature sequences shown. Thus, there is believed to be natively produced "long" basic FGF containing 154 amino acids, "primary" basic FGF containing 146 amino acids, and "short" basic FGF containing 131 amino acids. These FGFs are designated "basic" FGF, because they contain a high number of basic amino acid residues (lysine, arginine, histidine) and are therefore cations at neutral pH.

A protein is defined herein as basic FGF if it shows FGF activity in the foregoing assays, binds to heparin, is a cation at neutral pH, and reacts immunologically with antibodies prepared using a synthetic analog of the amino terminal sequence [tyr$^{10}$] FGF (1–10) conjugated to bovine serum albumin (if appropriate) or to other antibodies raised against bovine (or human) FGF or synthetic or native peptides thereof. See Baird, A., et al, *Regulatory Peptides* (1985) 10:309–317.

Acidic FGF has been isolated from bovine brain by others, and the first 34 amino acid residues determined. The cloning herein of the genes for bovine and human acidic FGF has permitted amino acid sequences additional to 1–34 for acidic bFGF, to be deduced as shown in FIG. 1a, and a partial sequence for acidic hFGF has been obtained, as shown in FIG. 2a. Subsequent to much of the work described below, the complete amino acid sequence for acidic bFGF was disclosed by Esch, et al, *Biochem Biophys Res Comm* (supra) and by Gimenez-Gallego, G., et al, *Science* (supra), as shown in FIG. 1b. Also, subsequent to most of the present work, the complete coding sequence for acidic hFGF was determined by the Maciag group, as shown in FIG. 2b.

The acidic protein also has two known active forms, one having the 140 amino acid sequence beginning at the phenylalanine residue numbered "1" in the figures, and a second shorter form corresponding to amino acids 7–140. Both the bovine and human proteins may also occur in N-terminal extended forms. Translation of DNA upstream of the codon for the amino acid numbered "1" in the figures (back to the ATG start codon at -15, shown in parentheses) represents the additional sequence of the extended protein. As is the case for basic FGF, the N-terminal methionine is almost certainly processed off in eucaryotic expression hosts, although it may not be if the gene is expressed in bacteria. Therefore, like the basic FGF described above, the native acidic protein may exist in three active forms: one truncated, i.e., "short," acidic FGF containing 134 amino acids; one N-terminal extended, i.e., "long" form containing 154 amino acids; and the other "primary" acidic FGF containing 140 amino acids beginning at the residue numbered "1" in the figures. It has been shown by Burgess, W. H., et al, (in press) that the bovine brain long form is blocked by an acetyl residue. These proteins contain a disproportionate number of acidic amino acid residues, i.e., glutamic and aspartic acids and the proteins are therefore anions at neutral pH.

A protein is defined herein as acidic FGF if it shows FGF activity in in vitro assays, binds to heparin, is an anion at neutral pH, and is immunologically reactive with antibodies prepared against human or bovine acidic FGF or against synthetic or native peptides thereof.

Acidic FGF and basic FGF are thus used herein to designate the foregoing proteins or proteins having amino acid sequences represented by those shown in FIGS. 1–4. Of course, these definitions are not restricted to the specific sequences shown, but include proteins which contain accidentally or deliberately induced alterations, such as deletions, additions, or exchanges of amino acid residues, so long as the biological activity, as measured by the foregoing in vitro and immunological assays, and respective anionic or cationic character at neutral pH does not change. Of course, modified forms may have slightly altered quantitative activity and specificity.

"Purified" or "pure" refers to material which is free from substances which normally accompany it as found in its native state. Thus "pure" acidic hFGF, for example, refers to acidic hFGF which does not contain materials normally associated with its in situ environment in human brain or pituitary. Of course, "pure" acidic hFGF may include materials in covalent association with it, such as glycoside residues.

"Operably linked" refers to a juxtaposition wherein the components are configured so as to perform their usual function. Thus, control sequences or promoters operably linked to a coding sequence are capable of effecting the expression of the coding sequence.

"Control sequence" refers to a DNA sequence or sequences which are capable, when properly ligated to a desired coding sequence, of effecting its expression in hosts compatible with such sequences. Such control sequences include at least promoters in both procaryotic and eucaryotic hosts, and optionally, transcription termination signals. Additional factors necessary or helpful in effecting expression may also be identified. As used herein, "control sequences" simply refers to whatever DNA sequence may be required to effect expression in the particular host used.

"Cells" or "cell cultures" or "recombinant host cells" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included in these terms, so long as the progeny retain the characteristics relevant to those conferred on the originally transformed cell. In the present case, for example, such a characteristic might be the ability to produce recombinant FGF.

B. General Description

Utility and Administration

The invention provides DNAs encoding growth factor proteins which are useful in encouraging the healing of wounds and which further may be supplied in sufficiently pure amounts to permit the design of inhibitors specific to them. The purified growth factors are generally applied topically to the traumatized tissue in order to stimulate vascularization and healing. Appropriate substrates are burns, wounds, bone fractures, surgical abrasions such as those of plastic surgery, or others requiring repair. Because application of these factors accelerates healing, they also reduce the risk of infection.

Indications wherein FGF is of value in encouraging neovascularization include musculo-skeletal conditions such as bone fractures, ligament and tendon repair, tendonitis, and bursitis; skin conditions such as burns, cuts, lacerations, bed sores, and slow-healing ulcers such as those seen in diabetics; and in tissue repair during ischaemia and myocardial infarction.

Formulations of the recombinantly produced growth factors using available excipients and carriers are prepared according to standard methods known to those in the art. The proteins can be formulated as lotions, gels, as part of a controlled release system, or ointments with additional active ingredients, such as antibiotics, if desired.

For topical administration, which is the most appropriate with regard to superficial lesions, standard topical formulations are employed using, for example, 0.1–10% solutions. Such solutions would be applied 3–6 times a day to the affected area. The concentration of the ointment or other formulation depends, of course, on the severity of the wound and nature of the subject. In most protocols, the dose is lowered with time to lessen likelihood of scarring. For example, the most severe wounds, such as third degree burns, are typically treated with a 10% composition, but as healing begins, the dose is progressively dropped to approximately 0.1% or lower, as the wound heals. A topical formulation for EGF using BSA as carrier was disclosed by Franklin, J. D., et al, *Plastic and Reconstruc Surg* (1979) 64:766–770.

For bone and tissue repair, administration is preferred locally, but by means of subcutaneous implant or slow release formulation implanted directly proximal the target. Surgery may be required for such conditions as bone injuries, thus making implantation directly practical. Slow-release forms can be formulated in polymers, such as Hydron (Langer, R., et al, *Nature* (1976) 263:797–799) or Elvax 40P (Dupont) (Murray, J. B., et al, *In Vitro* (1983) 19:743–747). Other sustained-release systems have been suggested by Hsieh, D. S. T., et al, *J Pharm Sci* (1983) 72:17–22), and a formulation specifically for epidermal growth factor, but not preferred in the present invention, is suggested by Buckley, R., *Proc Natl Acad Sci* USA (1985) 82:7340–7344.

As with topical administration, for sustained-release delivery, the concentration of FGF in the formulation depends on a number of factors, including the severity of the condition and the rate of FGF release from the polymer. In general, the formulations are constructed so as to achieve a constant local concentration of about 100 times the serum level of hormone or 10 times the tissue concentration, as described by Buckley et al (*Proc Natl Acad Sci* USA (supra)). Based on an FGF concentration in tissue of 5–50 ng/g wet weight (comparable to EGF at 60 ng/g wet weight), release of 50–5000 ng FGF per hour is acceptable. The initial concentration, of course, depends on the severity of the wound.

It is expected that FGF may act in concert, and even synergistically, with other growth factors such as epidermal growth factor (EGF), the transforming growth factors (TGF-α or TGF-β). insulin-like growth factors (IGF-1 and IGF-2), and/or platelet-derived growth factor (PDGF). In addition, specifically for bone repair, it may act in synergy with antagonists of parathyroid hormone, since parathyroid hormone promotes bone resorption. Therefore, also included within the compositions and administration protocols of the invention are embodiments wherein the FGF of the invention is administered in the same composition with, or in the same protocol with, one or more of the foregoing factors, thus more effectively to achieve the desired tissue repair.

Since FGF is effective in promoting neurite outgrowth, nerve regeneration, and neuronal survival, it may be useful for treatment of certain neurological disorders such as Alzheimer's and Parkinson's diseases, amyotrophic lateral sclerosis, and general aging of the nervous system, as well as traumatic injury to the spinal cord and peripheral nerves.

Administration of the drug for these indications is preferably by implant in formulations similar to those set forth above in connection with wound healing. The drug may also be delivered by means of implants of cell cultures as in transplant therapy by treating the cultures prior to transplantation with the FGF preparations of the invention. In addition, the FGF may be injected directly into the spinal fluid, or may be applied systemically. Systemic formulations are generally as are known in the art and include formulation in buffer or physiological saline, or other appropriate excipient. Dosage levels are approximately those of wound healing; however, for tissue culture or explant maintenance, it may be supplied at 0.1–10 ng/ml of serum or culture medium.

FGF proteins are particularly useful, also, in aiding the reformation and repair of tissues traumatized during surgery. For this use, it may be helpful to embed the FGF proteins in polymers used as surgical staples. The proteins are thus able to supplement biologically the mechanical suturing effected by the staples, and to augment and abet the "natural" healing processes in the repaired tissues.

In addition, it has been shown that angiogenic stimuli, such as those provided by the FGF proteins discussed herein, result in the release of tissue plasminogen activator (tPA) and of collagenase in vitro (Gross, J. L., et al, *Proc Natl Acad Sci* USA (1983) 80:2623–2627). Therefore, the FGF proteins of the invention are also useful in treatment of conditions which respond to these enzymes. While it may be necessary in acute situations (such as the presence of a blood clot associated with stroke or heart attack) directly to administer large doses of tPA to dissolve the clot, for treatment of chronic propensity to form embolisms, administration of FGF to maintain a suitable level of tPA in the blood stream may be desirable. Therefore, for this indication, systemic administration of the drug, using conventional means such as intramuscular or intravenous injection, is preferred.

The invention provides practical quantities of pure FGF growth factors for use in connection with the foregoing indications. Four specific endothelial growth factors are exemplified, each of which is apparently active in three forms: bovine acidic and basic FGF, and their human counterparts. Both acidic and basic factors are considered to occur in long, primary, and short forms, as described herein. It is considered that the N-terminal methionine of the long forms is processed off when the protein is produced in eucaryotic systems, and that the subsequent amino acid residue is derivatized, probably by acetylation, post-translation.

While FGF in its various forms does not have a recognized signal sequence, it must somehow be secreted, since it acts outside the cells producing it at a membrane-bound receptor. Therefore, while it is probably not secreted by the recognized constitutive secretion pathway, its secretion is accomplished by other means, such as by cell lysis or by exocytosis. For most tissues from which FGF is naturally derived, and for many mammalian expression systems, such release may be achieved by securing exocytosis with a calcium ionophore, such as the commonly employed A23187 (CalBiochem), which, in in vitro conditions, is added to the culture medium at 1–10 μM in the presence of 1 mM $CaCl_2$. For expression systems derived from macrophages or monocytes, other activation methods have been shown to be effective, such as the addition of lipopolysaccharide (LPS) at 10 μg/ml or the addition of *E. coli* endotoxin (Difco) (300 ng/ml). These stimulators have been shown to release the analogous factor interleukin-1 from macrophages by March, C. J., et al, *Nature* (1985) 315:641–647. These techniques can also be employed in releasing recombinantly produced FGF proteins when produced intracellularly without added signal sequences, as described below. Additional stimulators for release of intracellularly produced proteins include the phorbol esters and the triglycerides.

Gene Retrieval

The general strategy whereby the illustrated FGF-encoding sequences were obtained herein is as follows. The known N-terminal sequence of bovine acidic FGF was used to design a series of probes for use with a bovine genomic library ligated into phage. Phage recombinants which hybridized to the probes were isolated from the library and digested into smaller fragments suitable for cloning into M13 cloning vectors in order to obtain a "natural" probe. This resulted in an M13 probe containing a 250 bp sequence corresponding to a portion of the bovine acidic protein; this probe is central to recovering the complete coding sequences for the acidic forms of both bovine and human sources, as well as to obtaining the genes for the basic forms in these species.

Briefly, the fragments obtained by AluI digestion of a selected acidic bFGF gene fragment cloned into phage were shotgun cloned into M13 and a 250 bp fragment which hybridized to appropriate probe DNA selected and sequenced. The above, designated 250/AluI, was transferred into pBR322 and was used to probe a bovine brain, hypothalamus or pituitary cDNA library (to obtain the complete acidic bFGF sequence uninterrupted by introns) and a human genomic library (to obtain the first exon of the human acidic FGF genomic sequence). The middle and third exon of the human gene encoding acid FGF were obtained using oligomer probes, as described in the examples below. These probes were designed on the basis of a synthetic human acidic FGF gene. In addition, this same 250 bp fragment was used to design probes for the basic form, taking advantage of the available amino acid sequence information to alter the DNA to correspond to the basic rather than acidic form. The modified probe, thus designed on the basis of a comparison of the acidic bFGF N-terminal coding sequence and the basic bFGF amino acid sequence, was used to probe the same bovine pituitary cDNA library for the basic bFGF cDNA. The recovered bovine clone was then used to probe human genomic and cDNA libraries to recover the genomic sequence encoding human basic FGF-encoding DNA. Alternatively, the bovine cDNA clone λBB2 was mutagenized to convert the DNA sequence to one encoding the human form of the basic FGF protein. For both acidic and basic FGF, the cDNA and genomic clones described hereinbelow are useful in probing DNA libraries prepared from various species to obtain the analogous coding sequences from these mammalian libraries; in addition, the genomic clones are capable of expression in mammalian systems and may give better results than the corresponding cDNAs. cDNA libraries prepared from various tissues such as pituitary, brain, hypothalamus, or kidney can also be screened in this manner.

Expression of FGF Genes

The cloned genomic or cDNA sequences can be expressed in appropriate expression systems. Of course, for the DNAs disclosed herein, the foregoing protocol for retrieving them need not be repeated, but conventional chemical synthesis methods can suitably be employed. This permits adjustment of the DNA to obtain any desired form of the protein. cDNA sequences can be provided with appropriate controls suitable for any host, including bacteria, yeast, or eucaryotic cells. Reconstruction of the genomic sequences for human acidic FGF can be obtained from the three deposited λ phage harboring the three exons. Genomic sequences containing introns can be expressed using eucaryotic control sequences and eucaryotic hosts which are capable of splicing the transcripts. Vaccinia-based expression systems may also be used. Exemplary control sequence DNAs and hosts are given in paragraph C.1 below.

In particular, complete DNA encoding full length FGF can be constructed, for example, using a combination of recombinant and synthetic methods to obtain any of the long, primary or short forms of acidic or basic FGF. Heterologous signal sequences may also be fused to these, and advantage taken of the known relationship of the signal sequence to cleavage site to obtain the protein in the desired form. Intracellularly produced forms of the proteins can be obtained by cell lysis, or their release from the cells can be stimulated as described above. Particularly preferred are expression systems for either the cell-associated or putatively secreted (fused to signal sequence) forms which utilize control systems compatible with mammalian cells, such as CHO cells. Also preferred are vaccinia-based systems, which can be used for stable or transient expression in susceptible cells.

The recombinant FGF proteins thus produced are then purified in a manner similar to that utilized for purification of FGF from natural sources, but purification is considerably simpler, as the proteins form a much larger proportion of the starting material.

Polymorphism

It has also been shown that human genomic DNA exhibits a polymorphism in the region of the second exon of the gene. Existence of the polymorphism is a predictor of the tendency to solid tumors, as FGF is secreted by them, and probably is necessary for their survival, as it promotes blood vessel growth that keeps nutrients flowing to the tumor.

Figure 17:
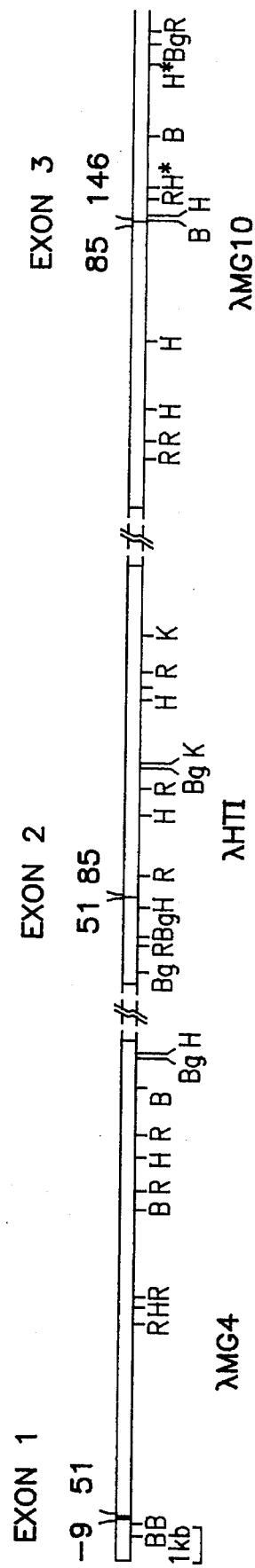
FIG. 17 shows a map of the human basic FGF encoding gene.

To detect the polymorphism, human genomic DNA is obtained by conventional methods, from a blood sample, for example, and subjected to size separation on polyacrylamide gels and probed using standard Southern blot techniques. An effective probe is the 1.4 kb EcoRI fragment obtained from the 2.1 kb insert into λBB2 described hereinbelow. When such a probe or its equivalent is used to hybridize to gels containing HindIII digests of the isolated human DNA, a 2.7 kb fragment is normally detected. In some individuals, an additional 2.9 kb fragment is also found. These fragments map to the region of the gene surrounding exon 2, as shown in FIG. 17.

Of three individuals tested, two exhibited only the 2.7 kb fragment; one exhibited both the 2.7 and 2.9 kb fragments. The hybridization intensity showed that the individual with both fragments contains both alleles, which is supported by results obtained by Southern blot analysis of DNA from mouse/human hybrid cell lines. In such hybrids, wherein only one chromosome is transferred, only one of the two fragments appears in each line.

C. Standard Methods

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

C.1. Hosts and Control Sequences

Both procaryotic and eucaryotic systems may be used to express the FGF encoding sequences; procaryotic hosts are, of course, the most convenient for cloning procedures. Procaryotes most frequently are represented by various strains of *E. coli;* however, other microbial strains may also be used. Plasmid vectors which contain replication sites, selectable markers and control sequences derived from a species compatible with the host are used; for example. *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the β-lactamase (penicillinase) and lactose (lac) promoter systems (Chang, et al, *Nature* (1977) 198:1056) and the tryptophan (trp) promoter system (Goeddel, et al *Nucleic Acids Res* (1980) 8:4057) and the lambda-derived $P_L$ promoter and N-gene ribosome binding site (Shimatake, et al, *Nature* (1981) 292:128).

In addition to bacteria, eucaryotic microbes, such as yeast, may also be used as hosts. Laboratory strains of *Saccharomyces cerevisiae,* Baker's yeast, are most used although a number of other strains or species are commonly available. Vectors employing, for example, the 2μ origin of replication of Broach, J. R., *Meth Enz* (1983) 101:307, or other yeast compatible origins of replication (see, for example, Stinchcomb, et al, *Nature* (1979) 282:39, Tschumper, G., et al, *Gene* (1980) 10:157 and Clarke, L, et al, *Meth Enz* (1983) 101:300) may be used. Control sequences for yeast vectors include promoters for the synthesis of glycolytic enzymes (Hess, et al, *J Adv Enzyme Req* (1968) 7:149; Holland, et al, *Biochemistry* (1978) 17:4900). Additional promoters known in the art include the promoter for 3-phosphoglycerate kinase (Hitzeman, et al, *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel, et al, 4,399, 216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV40) (Fiefs, et al, *Nature* (1978) 273:113), or other vital promoters such as those derived from polyoma, Adenovirus 2, bovine papilloma virus, or arian sarcoma viruses. The controllable promoter, hMTII (Karin, M., et al, *Nature* (1982) 299:797–802) may also be used. General aspects of mammalian cell host system transformations have been described by Axel (supra). It now appears, also that "enhancer" regions are important in optimizing expression; these are, generally, sequences found upstream or downstream of the promoter region in noncoding DNA regions. Origins of replication may be obtained, if needed, from vital sources. However, integration into the chromosome is a common mechanism for DNA replication in eucaryotes.

C.2. Transformations

Depending on the host cell used, transformation is done using standard techniques appropriate to such cells. The calcium treatment employing calcium chloride, as described by Cohen, S. N., *Proc Natl Acad Sci* (USA) (1972) 69:2110, or the $RbCl_2$ method described in Maniatis, et al, *Molecular Cloning: A Laboratory Manual* (1982) Cold Spring Harbor Press, p. 254 and Hanahan, D., *J Mol Biol* (1983) 166:557–580 may be used for procaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777–785 may be used. Transformations into yeast may be carried out according to the method of Beggs, J. D., *Nature* (1978) 275:104–109 or of Hinnen, A., et al, *Proc Natl Acad Sci* (USA) (1978) 75:1929.

C.3. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. Typical sequences have been set forth in ¶C.1 above. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleoside derivatives. The entire gene sequence for genes of sizeable length, e.g., 500–1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al, *Science* (1984) 223:1299; Jay, Ernest, *J Biol Chem* (1984) 259:6311.

Synthetic oligonucleotides are prepared by either the phosphotriester method as described by Edge, et al, *Nature* (supra) and Duckworth, et al, *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7 pmoles $\gamma$32P-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solution: in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/ chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 0.1–1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15–50 µl volumes under the following standard conditions and temperatures: for example, 20 mM Tris-Cl pH 7.5, 10 mM $MgCl_2$, 10 mM DTT, 33 µg/ml BSA, 10 mM-50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations are performed at 1 µM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per µg of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487–6500 and Adelman, J. P., et al, *DNA* (1983) 2:183–193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plagues which hybridize with the probe are then picked, cultured, and the DNA recovered.

C.4. Verification of Construction

In the constructions set forth below, correct ligations for plasmid construction are confirmed by first transforming *E. coli* strain MC1061 obtained from Dr. M. Casadaban (Casadaban, M., et al, *J Mol Biol* (1980) 138:179–207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci* (USA) (1969) 62:1159, optionally following chloramphenicol amplification (Clewell, D. B., *J Bacteriol* (1972) 110:667). Several mini DNA preps are commonly used, e.g., Holmes, D. S., et al, *Anal Biochem* (1981) 114:193–197 and Birnboim, H. C., et al, *Nucleic Acids Res* (1979) 7:1513–1523. The isolated DNA is analyzed by restriction and/or sequenced by the dideoxy nucleotide method of Sanger, F., et al, *Proc Natl Acad Sci* (USA) (1977) 74:5463 as further described by Messing, et al, *Nucleic Acids Res* (1981) 9:309, or by the method of Maxam, et al, *Methods in Enzymology* (1980) 65:499.

C.5. Hosts Exemplified

Host strains used in cloning and procaryotic expression herein are as follows:

For cloning and sequencing, and for expression of construction under control of most bacterial promoters, *E. coli* strains such as MC1061, DH1, RR1, C600hfl, K803, HB101, JA221, and JM101 were used.

D. Illustrative Procedure

The following examples are intended to illustrate but not to limit the invention. The DNA encoding the illustrated FGF sequences is obtained initially by screening a bovine genomic library and obtaining a pivotal probe, followed by retrieval of additional DNA. However, it would not be necessary to repeat this procedure, as the sequence of the pivotal probe is now known and could thus be constructed chemically in vitro. In addition, bacteriophage harboring the four illustrated sequences are deposited at the American Type Culture Collection.

EXAMPLE 1

Construction of the 250/AluI Probe:

Preparation of Acidic bFGF Genomic DNA

A 250 bp AluI bovine genomic fragment was used to probe both human and bovine libraries in order to obtain complete coding sequences for the illustrated acidic FGF proteins. This probe, designated 250/AluI, was obtained as follows.

The N-terminal amino acid sequence for residues 1–34 of bovine acidic FGF is known. Three long probes were prepared, based on codon choice (Anderson, S., et al, *Proc Natl Acad Sci* (USA) (1983) 80:6838–6842; Jaye, M., et al, *Nucleic Acids Res* (1983) 11:2325–2335) using an automatic synthesizer and a phosphoramidite coupling reagent. The sequences of these nucleotide probes are shown in FIG. 5. Probe 891 is a 48-mer corresponding to amino acids 1–16; probes 889 and 890 are 51-mers corresponding to amino acids 18–34 and are used as a 50–50 mixture of the two oligonucleotides which are identical except for the codon for arginine at position 24. The probes were used to screen a bovine genomic library obtained from Dr. Fritz Rottman, Case Western Reserve, which had been prepared as a partial MboI digest and was cloned into BamHI treated phage vector Charon 28 (Woychik, R. F., et al, *Nucleic Acids Res* (1982) 10:7197–7210).

Hybridization was conducted on denatured DNA replicated onto filters using a modification of the method described by Ullrich, A., et al, *EMBO J* (1984) 3:361–364; and the washing conditions were those of Wood, W. I., et al, *Nature* (1984) 312:330–337. Prehybridization/hybridization buffer contained 20% formamide, 5× Denhardt's solution (100× Denhardt's equals 2% bovine serum albumin, 2% polyvinyl pyrollidone; 2% Ficoll); 6× SSC (20× SSC equals 3M NaCl, 0.3M Na citrate); 50 mM sodium phosphate, pH 6.8; 100 µg/ml herring sperm DNA; hybridization buffer further included 10% dextran sulfate and about $10^5$–$10^6$ cpm/ml kinased probes 891 or 889/890. Prehybridization and hybridization were at 42° C. for 1 hr and 16 hr respectively. The filters were then washed 2× 15 min with 1× SSC, 0.1% SDS at 22° C., followed by 1 ten minute wash in 1× SSC, 0.1% SDS at 55° C. After washing, the filters were exposed for 1 day using intensifying screens.

The screened bovine genomic library contained 50 phage out of $10^6$ recombinants which hybridized to both probes. These 50 phage were further screened with mixtures of probes 853–856. In this screen, prehybridization/hybridization buffer contained 6× SBC, 1× Denhardt's, 0.1% SDB, 0.05% Na pyrophosphate, and 100 µg/ml salmon sperm DNA; hybridization buffer further contained $10^5$–$10^6$ cpm/ml probe. Probes 853–856 are 4 pools of 16 sequences each of the 64 (total) 17-mers corresponding to amino acids 7–12, synthesized using the phosphotriester method. However, 46 of the 50 clones further hybridized to the shorter probes. This hybridization was performed at between 65° C. to 35° C. for 16 hr and the base composition-independent washing method using tetramethyl ammonium chloride at 50° C. was used (Wood, W. I., *Proc Natl Acad Sci* (USA) (1985) 82:1585–1588).

Figure 6:
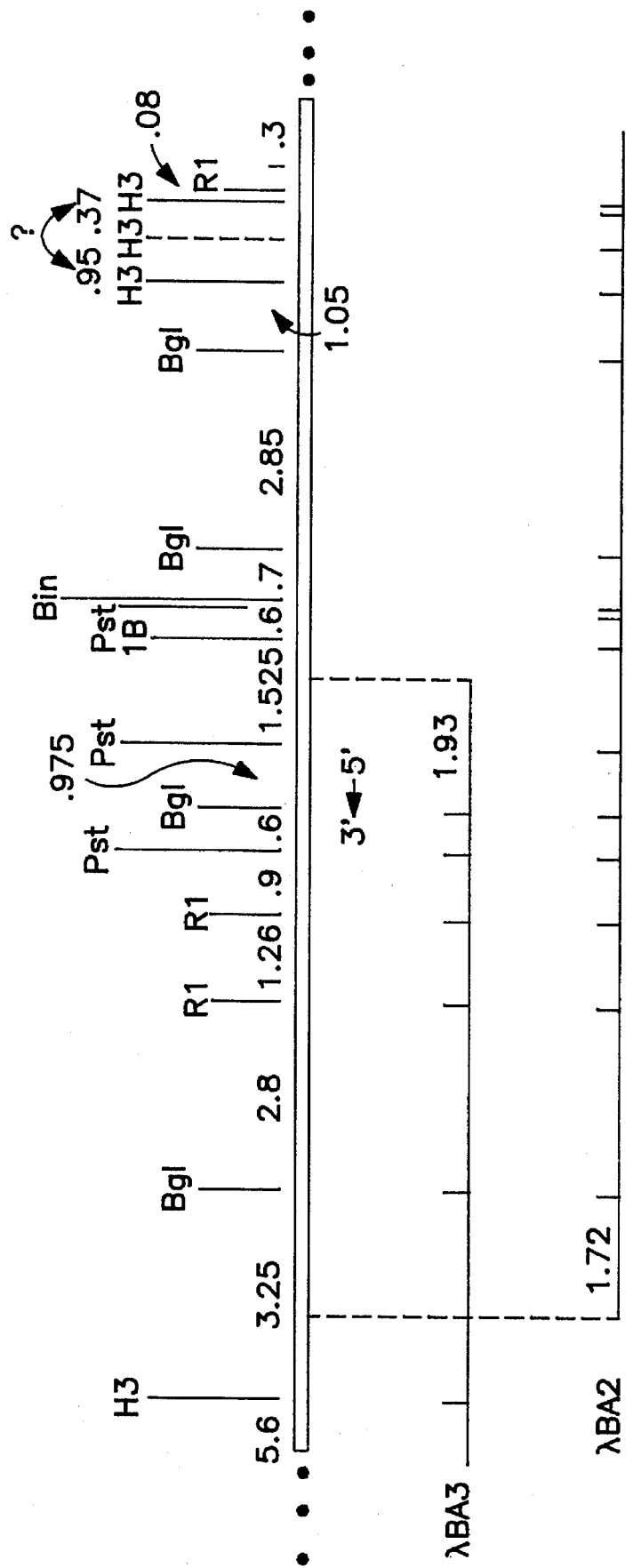
FIG. 6 gives restriction maps of the inserts for genomic acidic bFGF clones λBA2 and λBA3.

Two positively hybridizing phage were selected (λBA2 and λBA3) and the phage inserts were restriction mapped, as shown in FIG. 6, and partially sequenced as shown in FIG. 1a. Comparison of the deduced amino acid sequence with that published for the N-terminal 34 residues of the bovine acidic FGF native protein confirmed that these clones are correct. From the nature of the coding sequence it is apparent that amino acid residues 1–41 (as shown in FIG. 1a) are encoded in these clones; immediately subsequent nucleotides appear to represent an intron. The length of this intron is, at present, uncertain, but it, is possible that the complete acidic bFGF encoding sequence resides on these λBA2 and λBA3 DNAs. However any additional DNA required to obtain the complete coding sequences for this protein can be obtained from the same gene library using the λBA2 or λBA3 in "walking" techniques. The codons preceding the N-terminal residue are believed to encode the indicated fifteen amino acid prosequence, or, as discussed above, the "long" form of the native protein extended by fifteen amino acids at the N-terminus (or by fourteen if the N-terminal methionine is cleaved) as compared to isolated "primary" form.

To prepare the 250/AluI probe, λBA2 was partially digested with AluI and shotgun cloned into M13 (Messing, J., et al, *Gene* (1982) 19:269–276). The M13 plagues were hybridized in duplicate with 853–856 and 889/890. Phage hybridizing to both probes were sequenced. The resulting 250 bp AluI probe is shown in FIG. 7 along with the corresponding deduced amino acid sequence; its location on the λBA2 and λBA3 inserts of FIG. 6 corresponds to the site of probes 889/890 and 891. The 250/AluI probe corresponds to the N-terminal portion of the acidic bFGF protein.

EXAMPLE 2

Recovery of Acidic bFGF cDNA

The 250/AluI probe is used to retrieve the cDNA sequence encoding acidic bFGF. A cDNA library is obtained from bovine pituitary, brain, or hypothalamus mRNA using the λgt10 vector of Huynh, V. T., et al, *DNA Cloning Techniques: A Practical Approach* (IRL Press, Oxford, 1984). The resulting hybridizing clones permit recovery of the entire sequence encoding acidic bFGF.

Comparable cDNA libraries constructed using the analogous mRNA from other mammalian species is probed with the 250/AluI probe to obtain, for example, rat, ovine, bovine, feline, canine, equine, or porcine basic FGF.

EXAMPLE 3

Preparation of Acidic hFGF Genomic DNA

Figure 8:
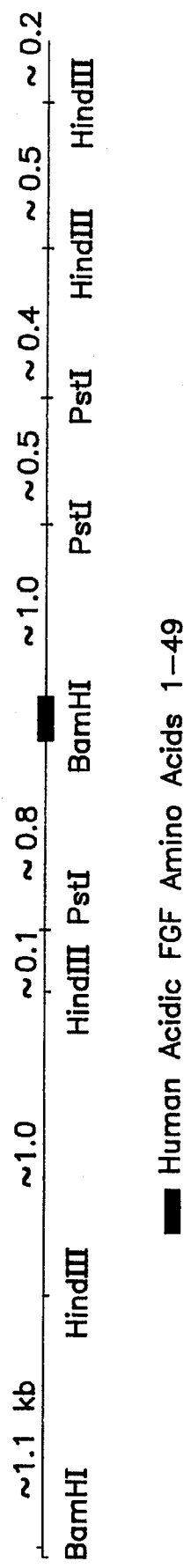
FIG. 8 is a restriction map of the insert in acidic hFGF genomic clone λHAG-9.1.

A human fetal liver genomic library in Charon 4A (Lawn, R. M., et al, *Cell* (1978) 15:1157–1174) was used as a source of the human sequences. The library was probed with nick-translated 250/AluI probe. The conditions of prehybridization/hybridization were the same as those for the 889/890 and 891 probes of Example 1. except that 40% formamide was used. Hybridization was at 42° C. for 16 hr. The filters were then washed at room temperature with 1× SSC, 0.1% SDS, and then for 2× 15 min at 50° C. with the same buffer. Positively hybridizing clones were cultured, and one, designated λHAG-9.1, contained the desired acidic hFGF sequences. A partial restriction map of this clone is shown in FIG. 8; nucleotide and amino acid sequence information is shown in FIG. 2a. The nucleotide sequence encoding amino acids 1–41 can be identified; this sequence, and, as in the genomic acidic bFGF, be followed by an intron. The acidic hFGF and bFGF amino acid sequences differ at positions 5, 21, and 35.

Human acidic FGF-encoding DNA also contains 15 codons preceding the N-terminus of the corresponding bovine isolated protein, which encode an amino acid sequence highly homologous to the N-terminal extension of the bovine protein. The translated sequence is shown in parentheses in FIG. 2a. In comparison to the bovine DNA, there are nucleotide substitutions in codons -3, -6, -9, and -12, which are silent in the translated protein. A nucleotide change in codon -10 results in the Thr residue of the bovine protein being an Ile residue in the human protein. Analogous to the bovine acidic FGF, this N-terminal extension may represent a prosequence or "long" form of the isolated, "primary" protein, either containing a fourteen or fifteen amino acid N-terminal extension depending on the fate of the methionine.

λ phage clones containing the nucleotide sequences corresponding to the middle and C-terminal encoding exons of the human acidic FGF-encoding genomic DNA were also obtained. Together with λHAG-9.1, described above, these phage provide the complete protein encoding sequence.

The phage containing the middle exon was obtained from a human genomic library prepared as described by Wyman, A. R. et al, *Proc Acad Natl Sci* (USA) (1985) 82:2880–2884. This is a library prepared by partial digestion of the human genome with Sau3AI and insertion of the resulting fragments into the polylinker region of λCharon 30 phage at the BamHI site. This places the insert between two EcoRI restriction sites for easy removal.

This genomic library was probed with two oligonucleotides which had been used to construct the synthetic human acidic FGF gene, as described in Example 4 immediately below, and illustrated in FIG. 9. The oligonucleotides designated "3" and "4" in that figure were those used as probes. The coding region of the recovered phage, designated λHG-3, is shown in FIG. 2b. This coding sequence encodes amino acids 42–85 of the Jaye sequence, and corresponds to the exon/intron boundaries of the gene encoding the basic FGF protein.

Similarly, the third exon was obtained from the Maniatis human genomic library of Lawn, et al, (supra) in Charon-4A, prepared as described above, and probed with oligonucleotides labeled "6" and "7" of the synthetic gene shown in FIG. 9. The retrieved λ-phage clone, designated λHAG-3, has been partially sequenced, and the results are shown in FIG. 2c. The sequence information also confirms the presence of the C-terminal exon sequence in the λHAG-3 insert.

The foregoing three inserts can be recombined to assemble the complete human acidic FGF genomic sequence by digestion of each phage with EcoRI to remove the insert and ligation of the resulting fragments to reconstruct the gene. The genomic sequence can then be used to construct expression vectors in a manner analogous to that described for cDNA sequences in Example 7 below. Specifically, the reassembled gene can be inserted as an EcoRI(blunt) fragment in a manner similar to that described for the Syn-acidic hFGF NcoI(blunt)/HindIII(blunt).

EXAMPLE 4

Preparation of Acidic hFGF Coding Sequence

A cDNA library prepared from human pituitary, breast carcinoma, brain, brainstem, SK-HEP-1, or hypothalamus mRNA by the method of Huynh, as described for the bovine mRNA in Example 2, is probed with the 250/AluI probe under the conditions described in Example 3 to obtain the cDNA encoding acidic hFGF. An unspliced cDNA containing the first exon was obtained from the breast carcinoma library.

In the alternative, the cDNA sequence information obtained by Jaye, M., et al, *Science* (1986), in press (see FIG. 2d), was used as a guide for the synthesis of a gene encoding the acidic hFGF. The cDNA clone reported by Jaye et al was obtained using messenger RNA from human brain stem and encodes an acidic hFGF whose deduced amino acid sequence is shown in FIG. 2b.

The genomic λHAG-9.1 clone described in Example 3 was used to provide the 5' portion of the gene. To prepare this portion, a 1.9 kb BamHI fragment was isolated from λHAG-9.1 and subcloned into pUC13 to obtain pCBI-101. This intermediate plasmid was then digested with NcoI/BamHI and the 118 bp fragment containing the codons for the 15 amino acids of the pro sequence along with the first 25 amino acids of the mature, "primary" form of acidic hFGF was isolated using a 5% polyacrylamide gel. The location of the NcoI site which contains the ATG that is believed to constitute the start codon at amino acid -15 from the beginning of the primary sequence, is shown in FIG. 9, which diagrams the synthetic gene.

The remainder of the coding sequence was synthesized using the synthetic oligonucleotides numbered 1–20 in FIG. 9. The synthesis of the individual oligonucleotides uses conventional automated techniques. The oligos were designed so as to yield the same nucleotide sequence as that reported by Jaye et al (supra) with two exceptions: oligonucleotides 4 and 14 were constructed so as to destroy the NcoI site spanning codon 67 by altering the GCC encoding alanine at codon 66 to GCT, as shown by the asterisk; in addition, oligonucleotides 19 and 20 were modified so as to add HindIII and EcoRI cleavage sites following the TGA termination codon. Neither of the foregoing changes affects the amino acid sequence encoded.

The synthetic oligonucleotides are ligated to obtain the sequence shown in FIG. 9 by kinasing 5 μg of each oligonucleotide (except #1 and #20) using standard reaction conditions, annealing the 10 different complementary oligonucleotide pairs (1+11, 2+12, etc.), and then ligating the ten oligonucleotide pairs into three segments. These segments are formed sequentially using T4 ligase under standard conditions. To obtain segment A, the pair 1/11 is ligated with 2/12, followed by ligation with 3/13, followed by ligation with 4/14. Segment B is formed by ligation of 5/15 with 6/16, followed by 7/17. Segment C is obtained by ligating 8/18 with 9/19, followed by ligation of the product with 10/20. The three ligated subfragments (A=144 bp, B=108 bp, and C=106 bp) are purified using gel electrophoresis and then sequentially ligated by mixing B and C under standard conditions with T4 ligase, followed by addition of A. The final reaction is extracted with phenol, precipitated with ethanol, the ethanol precipitate electrophoresed on a 5% acrylamide gel, and the 358 bp fragment A+B+C is eluted. The fragment spans the BamHI/EcoRI sites, as shown in FIG. 9, and its sequence is verified using dideoxy sequencing by subcloning the segment into M13mp19.

To complete the coding sequence, the synthetic 358 bp BamHI/EcoRI synthetic fragment is isolated from the phage or the polyacrylamide gel, its ends kinased, if necessary, and ligated to the 118 bp NcoI/BamHI fragment from pCBI-101. The resultant partially synthetic nucleotide sequence encoding acidic hFGF is shown in FIG. 9, and is designated Syn-acidic hFGF.

Of course, additional constructs wherein the "primary" and "short" forms of acidic FGF are immediately preceded by an ATG start codon, and contain a suitable restriction site might also be constructed.

EXAMPLE 5

Retrieval of Basic bFGF Genomic and cDNA Clones

The 250/AluI probe was then used to design appropriate probes to obtain the corresponding basic bFGF sequences. Advantage was taken of the finding of Esch, F., et al (supra) that amino acids 4–29 of acidic bFGF align with amino acids 13–38 of the basic bFGF sequence. Probes were designed based on the basic bFGF residues 18–36 and acidic bFGF residues 9–27, which regions are homologous at 14 of the 19 amino acids.

Probes 1097 and 1098, 40-mers designed to encode this region, were prepared using the phosphoramidite method on an automatic synthesizer. The probes are shown in FIG. 10; they overlap in the amino acid 23–31 region of the basic sequence. In designing the probes, the 250/AluI sequence was used where the amino acid sequence was the same, and where different, minimum nucleotide differences in order to effect the required change in encoded sequence were incorporated.

The bovine pituitary cDNA library obtained by the method of Huynh, V. T., as set forth in Example 2, was screened with 1098. Correct conditions for hybridization were determined using genomic DNA (Example 1) for Southern blot as follows:

It was, of course, expected that the 1097 and 1098 probes would cross-hybridize with acidic FGF encoding DNA under low stringency conditions. Southern blot analysis showed that genomic sequences known to encode acidic bFGF which hybridized to 1097 and 1098 at 55° C. wash temperatures failed to hybridize at 65° C. (Prehybridization/ hybridization buffer and conditions were as for 889/890 and 891 probes in Example 1.) Therefore, a wash temperature of 65° C. was chosen. At this temperature, a 10 kb fragment in an EcoRI digest and a 3.4 kb fragment in a PstI digest hybridized to probes 1097 and 1098.

Figure 11:
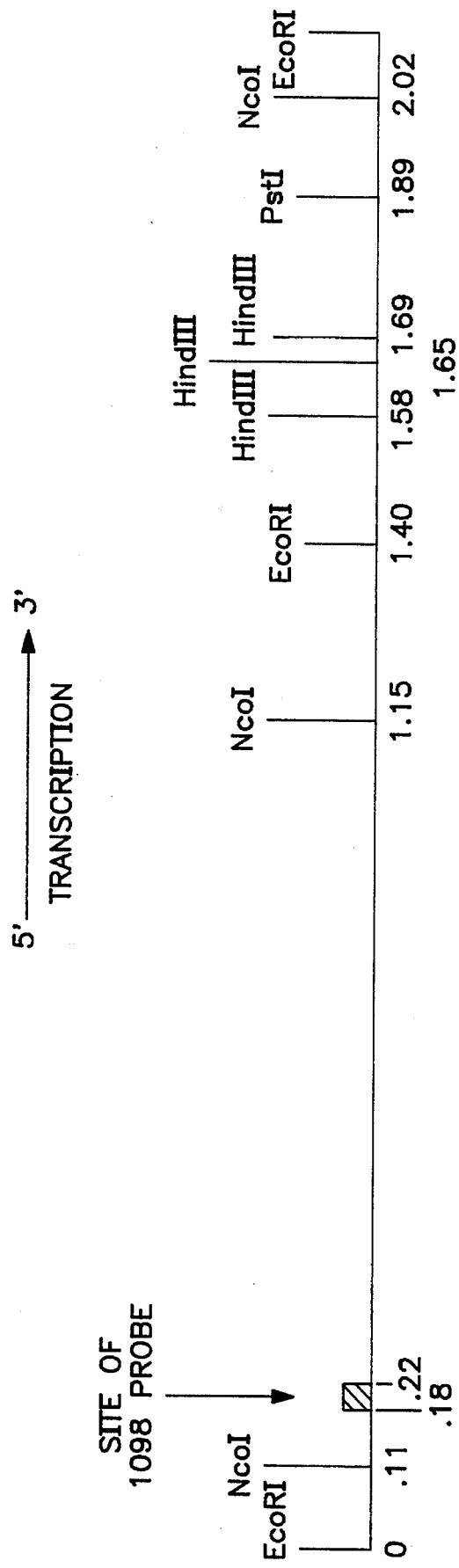
FIG. 11 is a restriction map of the basic bFGF cDNA clone λBB2.

When the cDNA library was probed as above using a 65° C. wash temperature, a single clone designated λBB2, representing a 2.1 kb cDNA with EcoRI linkers, was recovered. A restriction map of this phage is shown in FIG. 11. Subfragments of the insert in λBB2 were transferred to M13 for sequencing and a 1.4 kb EcoRI-digested subfragment was shown to encode amino acids 1–146 (the complete "primary" sequence) of bovine basic FGF. The sequence upstream from the N-terminal codon is believed to encode either a nine amino acid proseguence or an N-terminal extended "long" form of the native protein which retains activity. The N-terminal extension may contain only eight residues, of course, depending on whether the methionine is cleaved during post-translational processing. The portion of this subfragment encoding basic bFGF is shown in FIG. 3; amino acid numbering starting at position 1 corresponds to the N-terminus of the isolated "primary" protein. The upstream nine codons are translated in parentheses. The possibility that this extension represents an integral part of the native active protein is suggested by the higher MW form of the human basic FGF prepared from hepatoma cells by Klagsbrun, et al, *Proc Natl Acad Sci* (supra).

The 1.4 kb subfragment is then nick translated and used to screen a bovine genomic library constructed in a manner similar to that of Example 1 for the basic bFGF genomic sequences.

The 1.4 kb basic bFGF-encoding cDNA fragment is also used to probe alternate mammalian cDNA libraries, such as those from rat, pig, or bovine, feline, canine, equine or murine sources to obtain the basic FGF encoding sequences from these species.

EXAMPLE 6

Preparation of Human Basic FGF Genomic and cDNA Clones

A λgt10 cDNA library prepared from human kidney mRNA was also probed using the 1.4 kb bovine basic subfragment. Prehybridization/hybridization buffer contained 40% formamide, 5 mM Na phosphate, pH 6.5, 5× Denhardt's, 5× SSC, and 50 μg/ml herring sperm DNA; hybridization buffer also included 10% dextran sulfate and $10^4$–$10^5$ cpm/ml probe. Three clones were isolated, and one selected for characterization. This clone, designated λKB7, contained an approximately 1.4 kb EcoRI fragment which was partially sequenced to yield the data shown in FIG. 4, along with the deduced amino acid sequence. The sequenced coding region permits deduction of amino acids 1–50 shown in the Figure; the continuing sequence immediately downstream appears to represent the cDNA copy of an unspliced mRNA, indicating that an intron occurs in the basic FGF gene in a homologous position to the intron after amino acid 41 in the bovine and human acidic FGF genes. The λKB7 clone also provides upstream DNA encoding the nine amino acid N-terminal extension of the long form shown.

Additional genomic and cDNA libraries were screened using the same 1.4 kb basic bFGF-encoding fragment under precisely the same hybridization conditions as those employed for the human kidney λgt10 library above. Four additional clones were obtained, which between them encode the entire 146 amino acid protein corresponding to the isolated basic bFGF, as shown in FIG. 4. Nine upstream codons included in λKB7 above translate into a sequence having complete homology with the translated upstream codons in the bovine basic FGF clone, although there is a silent nucleotide substitution in codon -8. This translated N-terminal extension is shown in parentheses in FIG. 4; and, as above, may represent a prosequence or the additional amino acids of an N-terminal extended active protein.

In more detail, two positively hybridizing clones from a human genomic library in λ Charon 4A, prepared as described by Lawn, R. M., et al (supra) were designated λMG4 and λMG10, λMG4 encodes amino acids (-9)-51; λMG10 encodes amino acids 86–146, representing the third of three exons contained in the mature protein-encoding region of the gene. (The location of exon/intron boundaries was determined by homology to the bovine sequence.) A slightly different genomic library in λ Charon 28, obtained from E. Fritsch, yielded λHT1 which contains the second mature protein exon, encoding amino acids 51–85. Finally, λHFL1, a cDNA clone obtained from a human fetal liver library prepared in λgt10 as described above, encodes amino acids 56–146, confirming the location of the relevant intron/exon junction.

There are only two amino acid differences between basic bFGF and hFGF, at position 112, where the bovine protein has Ser and the human protein has Thr, and at position 128, where the bovine protein has Pro and the human has Ser. These differences are the result of a single nucleotide difference in each case; therefore bovine cDNA may conveniently be modified by site directed mutagenesis as described below to encode the human protein, and, indeed, standard site-specific mutagenesis techniques were used to alter these codons. The λBB2 clone of Example 5 was digested with EcoRI and the 1.4 kb region spanning the bFGF protein-encoding portion was ligated into the EcoRI site of M13mp8. The in vitro mutagenesis was carried out in the presence of three oligonucleotides: the "universal" primer, a 17-mer; the mutagenic 16-mer 5'-GAAATACAC-CAGTTGG-3'; which alters the coding sequence at codon 112, and the mutagenic 17-mer 5'-ACTTGGATCCAAAA-CAG-3', which alters the sequence at codon 128. The mutagenized phage was also subjected to a second round of in vitro primer-directed mutagenesis to create a HindIII site 34 bp downstream from the translation termination codon using the mutagenic 25-mer, 5'-TTTTACATGAAGCTT-TATATTTCAG-3'. The resultant mutated DNA was sequenced by dideoxy sequencing to confirm that the desired mutagenesis had occurred, and the approximately 630 bp fragment spanning the FGF coding region was excised with HindIII and ligated into pUC13 to obtain the intermediate plasmid pJJ15-1.

Of course, modified forms of the coding sequence to encode any of the three known N-terminal modifications of basic FGF may also be prepared by using standard synthesis techniques.

EXAMPLE 7

Construction of Expression Vectors and Stable Expression of FGF in Mammalian Cells The cDNA clones encoding FGF are most conveniently used to produce the recombinant proteins in a variety of hosts, as set forth in ¶C.1 above. However, expression in mammalian systems is favored as the host is capable of post translational processing analogous to that experienced by the natively produced protein, and either cDNA or genomic sequences may be used, as the host is also capable of processing introns.

Thus, a full-length cDNA or genomic FGF encoding clone is prepared for insertion into a host vector, illustrated by, but not limited to, those described below.

To construct the vectors, the cloned FGF-encoding insert is excised with EcoRI (by partial digestion if the insert itself contains EcoRI sites), or other appropriate enzyme, provided with EcoRI or other appropriate linkers if necessary, and then inserted into an appropriate host vector such as pHS1 or its derivatives as described below.

Construction of Host Vectors pHS1

The plasmid pHS1 is suitable for expression of inserted DNA in mammalian hosts. It contains 840 bp of the hMT-II sequence from p84H (Karin, M., et al, *Nature* (1982) 299: 297–802) which spans from the HindIII site at position -765 of the hMT-II gene to the BamHI cleavage site at base +70. To construct pHS1, plasmid p84H was digested to completion with BamHI, treated with exonuclease BAL-31 to remove terminal nucleotides, and then digested with HindIII. The desired 840 bp fragment was ligated into pUC8 (Vieira, J., et al, *Gene* (1982) 19: 259–268) which had been opened with HindIII and HincII digestion. The ligation mixture was used to transform *E. coli* HB101 to Amp$^R$, and one candidate plasmid, designated pHS1, was isolated and sequenced by dideoxy sequencing, pHS1 contains the hMT-II control sequences upstream of a polylinker containing convenient restriction sites.

The workable host plasmid pHS1 can be further modified to contain additional control elements besides the metallothionein promoter. In particular, the enhancer elements of vital systems, such as SV40, can be included, as well as termination signals associated with the 3' untranslated regions of other proteins such as hGH.

Vital Enhancer

A pair of host expression vectors containing the SV40 enhancer in operable linkage to the MT-II promoter was constructed by inserting an 1120 bp SV40 DNA fragment into the HindIII site preceding the MT-II promoter sequences in pHS1. The SV40 DNA fragment spans the SV40 origin of replication and includes nucleotide 5171 through nucleotide 5243 (at the origin), the duplicated 72 bp repeat from nucleotide 107–250, and continues through nucleotide 1046 on the side of the origin containing the 5' end of late vital mRNAs. This HindIII 1120 bp fragment is obtained from a HindIII digest of SV40 DNA (Buchman, A. R., et al, *DNA Tumor Viruses,* 2d ed (J. Tooze, ed.), Cold Spring Harbor Laboratory, New York (1981), pp. 799–841), and cloned into pBR322 for amplification. The cloning vector was cut with HindIII, and the 1120 bp SV40 DNA fragment isolated by gel electrophoresis and ligated into HindIII-digested, CIP-treated, pHS1. The resulting vectors, designated pHS1-SV(9) and pHS1-SV(10), contain the fragment in opposite orientations preceding the MT-II promoter. In pHS1-SV(9), the enhancer is about 1600 bp from the 5' mRNA start site; in the opposite orientation it is approximately 980 bp from the 5' mRNA start site. Both orientations are operable, but the orientation wherein the enhancer sequences are proximal to the start site provides higher levels of expression. It is believed that deletions which place the enhancer 250–400 bp upstream of the transcription start are optimal.

Additional vectors were constructed which place the SV40 enhancer 3' terminus 190 bp, 250 bp, and 360 bp respectively upstream from the 5' end of the MT promoter TATA box. The constructions were based on the mapping of the upstream regulatory regions of the human MT promoter described by Karin, M., et al, *Nature* (1984) 308:513–519. All constructions retain the sequences containing the duplicated sites for regulation by heavy metals, but the constructions with the 190 bp and 250 bp separations do not retain the sequence for glucocorticoid regulation which is further upstream from these sites.

These vectors, designated pHS'-SV190, pHS'-SV250, and pHS'-SV360 are prepared as follows; all constructions are identical except for the length of sequence containing the metallothionein promoter and upstream region which is supplied as a fragment excised from pHS1.

For pHS'-SV190, pHS1 is digested with SacII, blunted, and ligated to KpnI linkers. The DNA is then digested with EcoRI and KpnI to liberate the appropriate portion of the MT-II control sequences. Similarly, for pHS'-SV250, pHS1 is digested with HgaI, blunted, ligated to KpnI linkers and digested with EcoRI and KpnI; for pHS'-SV360, DdeI is used in the initial digestion.

An intermediate vector containing the SV40 enhancer is prepared by inserting the HindIII/KpnI fragment of SV40 (which extends from position 5171 to position 294 and which contains the enhancer element 50 bp from the KpnI site) into KpnI/HindIII digested pUC19 to obtain pUC-SV. (pUC19 contains three convenient restriction sites in the polylinker region, in order, HindIII, KpnI, and EcoRI.) The finished vectors are obtained by inserting the KpnI/EcoRI fragments prepared as described above into KpnI/EcoRI digested pUC-SV.

All of the foregoing modified vectors, thus, take advantage of the SV40 enhancer element. Other vital enhancers could, of course, be used in an analogous manner.

Transcription Termination Sequences

To provide transcription termination control sequences, DNA representing the coding sequence and 3' untranslated sequence of human growth hormone was ligated into pHS1. The intermediate vector can provide the hGH 3' untranslated sequence to coding sequences subsequently ligated into the vector in place of the hGH coding sequence.

The genomic sequences encoding hGH were isolated from p2.6-3 (DeNoto, et al, *Nucleic Acids Res* (1981) 19:3719) by digestion with BamHI, which cuts at the 5' end of the first exon, and EcoRI, which cuts 3' of the functional gene, followed by polyacrylamide gel purification. The isolated fragment was ligated into BamHI/EcoRI digested pHS1 and the ligation mixture transformed into *E. coli* MC1061 to Amp$^R$. Successful transformants were screened by restriction analysis, and a strain containing the desired plasmid, pMT-hGHg, was further propagated to prepare quantities of plasmid DNA.

In a manner similar to that described above for constructing pHS1-SV(9) or pHS1-SV(10), but substituting for pHS1, pMT-hGHg, a pair of vectors containing the hGH gene under the control of the MT promoter, and operably linked to SV40 enhancer, and designated, respectively, phGHg-SV(9) and phGHg-SV(10), were obtained. The ligation mixtures were used to transform *E. coli* 1061 to Amp$^R$. and the correct constructions verified.

Construction of Expression Vectors phGHg-SV(10) was then used as a host vector to accommodate Syn-acidic hFGF. phGHg-SV(10) was digested with BamHI and SmaI, blunted with Klenow, and treated with CIP to excise the hGH coding sequence. This opened vector was ligated to the NcoI(blunt)/EcoRI(blunt) Syn-acidic hFGF fragment to obtain the desired expression vector pahFGF-SV(10), in which the NcoI site of the Syn-acidic hFGF fragment is recreated.

Similarly, the remaining FGF-encoding fragments described above are ligated into phGHg-SV(10) to prepare analogous vectors containing these coding sequences under control of the vital enhancer, MT-II promoter and the hGH 3' untranslated regions. For example, the -500 bp NcoI (blunt)/HindIII (blunt) fragment from pJJ15-1 of Example 6 is conveniently inserted into BamHI (blunt)/SmaI-digested phGH-SV(10) to obtain pJJ16-2.

In addition, other host vectors may be used to obtain expression of these sequences, including pHS1 and pHS1 modified to contain the various configurations of SV enhancer as above described. Insertion is by analogous means, using BamHI/EcoRI digestion of the host vector. Also, DNA modified to encode any of the "long", "primary" or "short" forms of the acidic or basic FGF may be employed.

These vectors are generically designated pMT-FGF for the purposes of the discussion below.

Production of FGF by Mammalian Recombinants

Chinese hamster ovary (CHO)-K1 cells were grown on medium composed of a 1:1 mixture of F12 medium and DME medium with 12% fetal calf serum. The competent cells were co-transformed with pMT-FGF and pSV2:NEO (Southern, P., et al. *J Mol Appl Genet* (1982) 1:327–341). pSV2:NEO contains a functional gene conferring resistance to the neomycin analog G418. In the transformation, 500 ng of pSV2-NEO and 5 µg of pMT-FGF were applied to a 16 mm dish of cells in a calcium phosphate-DNA co-precipitate according to the protocol of Wigler, M., et al, *Cell* (1979) 16:777–785, with the inclusion of a two minute "shock" with 15% glycerol after four hours of exposure to the DNA. A day later, the cells were subjected to 1 mg/ml G418 to provide a pool of G418-resistant colonies, which were assayed for FGF production and then can be cloned out.

Successful transformants, also having a stable inheritance of pMT-FGF, are plated at low density for purification of clonal isolates. Small amounts of these isolates are grown in multi-well plates after exposure to $10^{-4}$M zinc chloride for convenient assay of FGF production. FGF determinations are made by standard ELISA or radio-immunoassays against the antisera prepared against the appropriate FGF protein using standard methods. Clonal isolates which produce large amounts of the desired FGF are selected.

The cells, which have been shown to produce FGF under suitable conditions, are seeded at 1/10 confluency in basal medium supplemented with 10% fetal calf serum, incubated overnight, and then induced for FGF production by addition of zinc chloride in the concentration range of $1 \times 10^{-4}$M to $3 \times 10^{-4}$M. FGF levels rise for 7–10 days, under optimal inducing conditions, $2 \times 10^{-4}$M ZnCl$_2$.

In a particular experiment, CHO cells were transformed using pMT-FGF containing the approximately 500-bp NcoI-(blunt)/HindIII(blunt) fragment encoding human basic FGF derived from pJJ15-1 of Example 6. This fragment was inserted into BamHI(blunt)/SmaI-digested phGH-SV(10), as described above, to obtain this particular form of pMT-FGF (designated pJJ16-2, hereinabove). The cells were cotransformed with this vector, pSV-neo, and pHS1-MT. After G418 selection, the pooled resistant colonies produced approximately 500 pg of human basic FGF per $10^6$ cells.

The amount of FGF produced was determined by affinity-purifying the basic FGF from lysed cells using heparin-Sepharose, followed by assay for growth promotion of endothelial cells in tissue culture. The heparin affinity purification is performed by standard methods such as those described, for example, by Sullivan, R., et al, *J Biol Chem* (1985) 260:2399–2403, or by Shing, et al, *Science* (1984) 223:1296–1299, and the activity assay was performed using procedures as described by Gospodarowicz, D., et al, *J Cell Physiol* (1985) 122:323–332, or Gospodarowicz, D., et al, *J Cell Biol* (1983) 97:1677–1685.

The foregoing pools, producing at a level of 500 pg/$10^6$ cells, were then selected for cadmium resistance by growing them in the presence of 10 µM CdCl$_2$ with 100 µM ZnCl$_2$ as inducer. Pools of resistant clones were then assayed, as described above. Production levels of 5.6 ng/$10^6$ cells were found one assay.

If desired, the FGF can be obtained from the lysed cells and purified according to the procedures set forth above for the native protein, or by other standard methods known in the art.

In addition, as discussed above, secretion of the FGF proteins produced by the foregoing constructs can be achieved by exocytosis initiated by a calcium ionophore or other suitable stimulant. While it is not expected that proteins produced by CHO cells, specifically, would be released by LPS or phorbol ester stimulation, for example, by substituting for CHO cells, cell lines derived from macrophage as recombinant hosts, such secretion can be effected. Also, by altering the construction so as to provide a signal sequence, such as that exemplified below, derived from hGH, secretion using the normal constitutive pathways could also be effected using CHO or other mammalian cell hosts. Effecting secretion has some advantages, of course, since the protein purification task becomes much simpler.

Transfection with a pMT-FGF vector containing the Syn-acidic hFGF partially synthetic sequence will result in the production of "long" FGF containing the 14 amino acid pro region upstream of the 140 amino acids of the mature primary form; the processed Met residue may also be replaced with a blocking group such as acetyl. Processing may also occur in mammalian cells to result in the mature form; however, it is established that the long form containing the leader sequence minus the initiating Met, and with the now N-terminal alanine residue acetylated, is active as a mitogen.

In any event, FGF is partially purified by passage over heparin/sepharose, and elution with 1.2M NaCl for acidic FGF and 2M NaCl for basic FGF. The eluate is analyzed for the presence of acidic or basic FDF by SDS-PAGE and by mitogenic activity on endothelial or 3T3 cells.

EXAMPLE 8

Construction of Vaccinia Vectors for Human FGF and Transient Expression in CV-1 Cells The basic hFGF-encoding sequences were provided with the 3' untranslated region from hGH by digesting phGH-SV(10) (supra) with BamHI and SmaI, blunting with Klenow, and inserting the approximately 500 bp NcoI (blunt)/HindIII (blunt) fragment spanning the FGF from pJJ15-1. The resulting plasmid, pJJ16-2, can be used directly as an expression vector, as described above.

However, the NcoI/EcoRI fragment (approximately 1.1 kb) containing the basic bFGF coding region and the hGH polyA addition signal was purified on a 5% acrylamide gel, eluted, blunted with Klenow, and ligated into SmaI-digested phosphatased pGS20 (Mackett et al, *J Virol* (1984) 49:857–864). The resulting plasmid, designated pJV1-1, was amplified in *E. coli* MC1061, and the plasmid DNA was isolated using a cesium chloride gradient.

The Syn-acidic hFGF DNA fragment synthesized in Example 4 is also ligated into the vaccinia transient expression vector pGS20. The Syn-acidic hFGF gene shown in FIG. 9 is cut with NcoI and EcoRI, blunted with Klenow and ligated into SmaI-cut phosphatased pGS20. The resulting plasmid preparation is purified by centrifugation to equilibrium in cesium chloride to recover the recombinant plasmid designated pJV1-2.

The pJV1-1 and pJV1-2 vectors are transformed into CV-1 cells infected with vaccinia, as described by Cochran, M. A., et al, *Proc Natl Acad Sci* (USA) (1985) 82:19–23.

Figure 12:
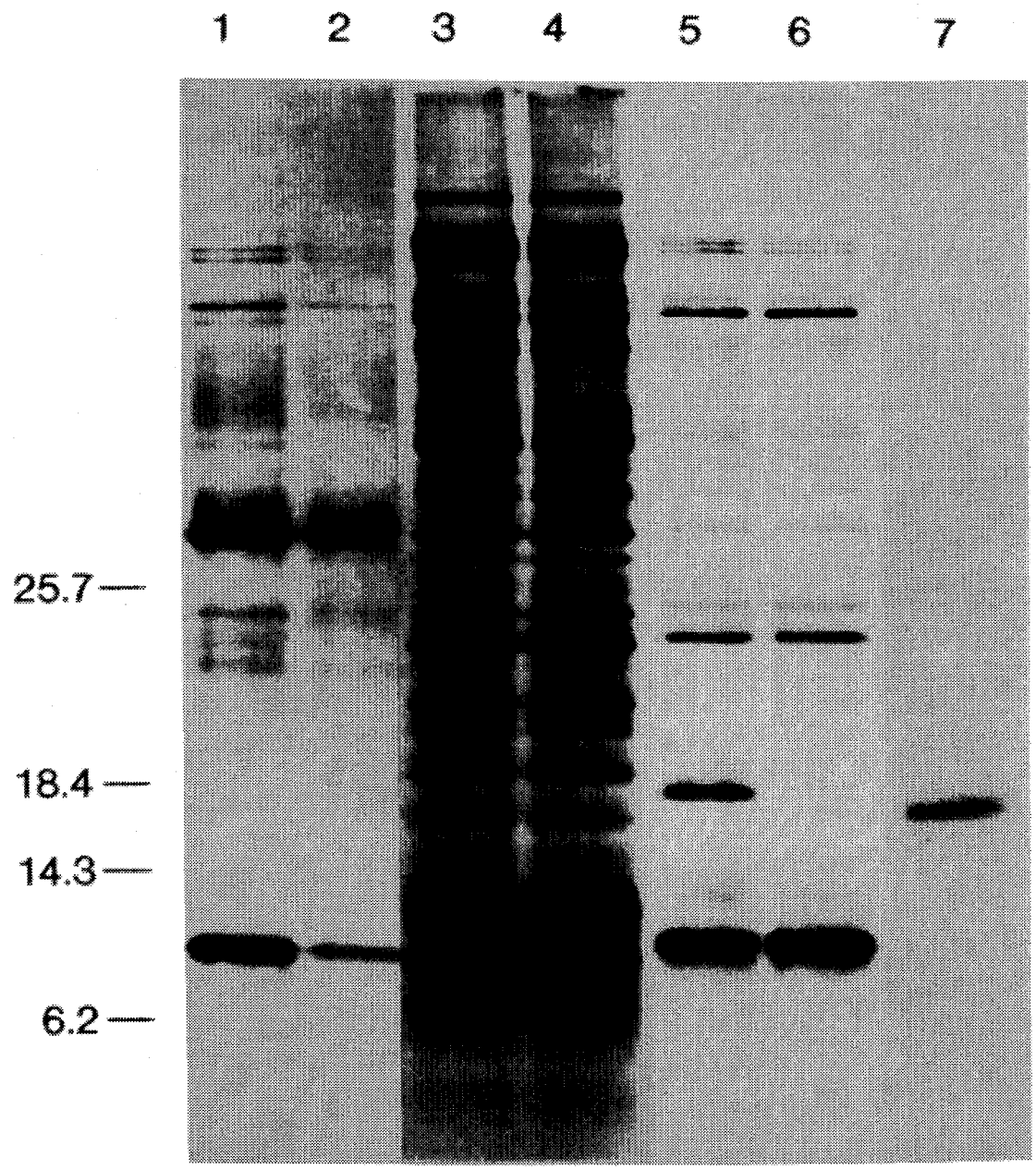
FIG. 12 shows the results of transient expression of basic hFGF in CV-1 cells.

CV-1 cells transfected with pJV1-1 or pGS20 were assayed for the production of basic hFGF using SDS-PAGE autoradiography. The results are shown in FIG. 12. Lanes 1 and 2 are the media of cells transfected with pJV1-1 and pGS20 respectively, lanes 3 and 4 are samples of the corresponding cell lysates, and lanes 5 and 6 are the same as lanes 3 and 4 except that the samples of lysate were bound to heparin sepharose in the presence of 0.6M NaCl, washed with 10 mM phosphate, pH 7.4/1.1M NaCl, and eluted from the column with 2M NaCl in the same buffer. (The eluates were precipitated with TCA before loading on the gel.) Lane 7 is $^{125}$I-labeled basic FGF in the 146 amino acid form. The band at approximately 18 kd in lane 5, which has a slightly higher molecular weight than the FGF standard, shows that the "long" form of the bovine sequence is formed in preference to the "primary" protein obtained from tissues.

Samples prepared as described for lanes 5 and 6 (except for the TCA precipitation) were also tested for mitogenic activity on bovine brain capillary endothelial cells. (See Example 9.) No activity was present in the pGS20 sample, but the pJV1-1 sample contained activity equivalent to 20 pg FGF/µl.

EXAMPLE 9

In Vitro Assay for FGF

The assay was performed substantially as described by Esch et al, *Proc Natl Acad Sci* (USA) (1985) 82:6507–6511; and by Gospodarowicz et al, *J Cell Physiol* (1985) 122:323–332.

Briefly, bovine brain capillary endothelial cells were maintained in the presence of DMEM supplemented with 10% calf serum. Monolayers were dissociated by exposure to a solution containing 0.9% NaCl, 0.01M sodium phosphate, pH 7.4, 0.05% trypsin, and 0.02% EDTA for 2–3 minutes at room temperature. After the cells had rounded up, they were resuspended in DMEM and 10% calf serum and an aliquot of the cell suspension was counted in a Coulter counter. The cells were seeded at an initial density of 2×10$^4$ cells per 35 mm dish, each dish containing a total of 2 ml DMEM plus 10% calf serum. Six to twelve hours later, a set of duplicated plates was trypsinized and cells were counted to determine the plating efficiency.

Aliquots of the sample to be tested for FGF activity were diluted 1:2, 1:4, and 1:8 with DMEM plus 0.5% BBA, and 10 µl of the dilutions were added to triplicate assay plates on days 0 and 2. On day 4, the triplicate plates for each sample dilution were trypsinized and the cell densities determined by Coulter counter.

EXAMPLE 10

Expression of Signal Sequence Fusions

Since the recombinant forms of FGF were not found in the medium of CHO or CV-1 cells, the FGF-encoding DNA sequences are also ligated to a heterologous signal sequence in order to effect the secretion of the recombinant FGF protein. The fused sequences are then ligated into vaccinia-based vectors to effect transient expression and secretion in vaccinia-infected CV-1 cells, or into pHS1 based vectors for expression and secretion in CHO cells.

The signal sequence from human growth hormone was obtained from the cDNA vector chG H800/pBR322 of Martial, J. A., et al, *Science* (1979) 205:602–607, as an 800 bp HindIII fragment which includes all of the coding sequence. An NaeI restriction site is placed immediately 3' of the 26 amino acid signal-encoding DNA by site-specific mutagenesis so that subsequent cleavage by NaeI results in a fragment with a blunt-end immediately after the codon for the alanine residue which is at the C-terminus of the signal sequence. In summary, the HindIII fragment is ligated into M13mp19 and mutagenized using the primer: 5'-ATGGT-TGGGCCGGCACTGCC-3', and the mutagenized sequences recovered and digested with BamHI and NaeI to give the signal sequence-containing fragment.

(Properly tailored forms of the β-lactamase signal sequence could also be used in analogous constructions (Lingappa, V. R., et al, *Proc Natl Acad Sci* (USA) (1984) 81:456–460).)

DNAs encoding four forms of basic hFGF are supplied as partially synthetic fragments each containing a constant C-terminal fragment from the altered λBB2 clone described above and a variable synthetic N-terminal portion. For the C-terminal position, the altered λBB2 clone is digested with HhaI, which cuts 122 bp downstream from the initiating methionine codon, and with HindIII, to obtain a 377 bp subfragment extending to the HindIII site in the 3' untranslated region. The missing portions upstream from the HhaI site are supplied using synthetic oligonucleotides.

The synthetic oligonucleotides are shown in FIG. 13. They are synthesized and ligated in a manner analogous to that described above in connection with the production of Syn-acidic hFGF. The individual oligonucleotides are synthesized using a standard automated nucleic acid synthesizer, annealed, and the double-stranded portions ligated to form the pertinent entire upstream portion containing a HhaI site at its 3' end. These synthetic upstream fragments are then ligated using T4 ligase to the downstream HhaI/HindIII fragment to obtain the entire FGF gene, and then ligated to the hGH BamHI-NdeI fragment to add the hGH signal sequence coding region.

The hGH/basic FGF protein junctions encoded by the synthetic upsteam portions are shown in FIG. 14. Protein A contains the reconstructed upstream portions and ligated C-terminal codons thus encoding amino acids -9 to 146. shown in FIG. 4, the total of 155 amino acids thus encoding the long form of basic human FGF. Protein B contains the same sequence, except that the N-terminal methionine at -9 has been replaced by an alanine residue. Protein C encodes amino acids 12–146 of FIG. 4, and protein D encodes amino acids 16–146 of this protein, i.e., the "short" form of human basic FGF, which is already known to show mitogenic activity.

FIG. 14 also shows the predicted signal sequence cleavage sites (in heavy arrows) for the immediate expression product, according to the rules set forth by von Heijne, G., *Eur J Biochem* (1983) 133:17–21.

To complete the constructions, the fragments encoding the four proteins fused to hGH signal sequence set forth in FIG. 14 are inserted into carrier plasmid pUC9 for amplification as a BamHI(partial)/HindIII sequence and correct construction is confirmed by dideoxy sequencing. The BamHI(partial)/HindIII confirmed sequence fragment is then excised from the carrier plasmid, blunted with Klenow, and ligated into the SmaI site of pGS20 (supra), and the ligated recombinant plasmid expressed in vaccinia-infected CV1 cells, as described above.

Analogously, constructs are made of acidic hFGF for secretion in similar expression systems. The FGF-encoding sequences are derived from the Syn-acidic hFGF DNA fragment, modified to produce proteins E, F, and G in FIG. 15, which represent, respectively, hGH/acidic FGF protein junction regions of the long form of acidic FGF spanning the residues -15 to 140 of FIG. 2b, the primary form represented by residues 1–140 of FIG. 2b, and the short form spanning residues 7–140 of that figure, all with minor changes in the FGF amino-terminus, as shown in the figure.

To construct these FGF-encoding sequences, the NcoI/EcoRI Syn-acidic FGF is blunted with Klenow at the NcoI site and ligated into SmaI/EcoRI-digested M13mp19. The resultant phage is mutagenized with the oligonucleotide: 5'-GTAATTCCCGGGAGGCAGAT-3', thus creating a SmaI site at nucleotide position 62 of FIG. 9 immediately before the codon for the glycine, which is residue 6 of the primary acidic hFGF. Digestion of the mutagenized fragment with SmaI and EcoRI provides a 414 bp fragment, which is either ligated directly to the BamHI/NaeI hGH signal-encoding fragment to obtain a DNA encoding a recombinant form shown as protein G in FIG. 15, or is first ligated to the synthetic oligonucleotides (shown in FIG. 16) and then to the BamHI/NaeI fragment to obtain the sequences encoding the peptides designated E and F in FIG. 15.

In a manner exactly analogous to that set forth above for human basic FGF, the signal sequence-preceded acidic FGF DNA fragments are disposed in pGS20 and transfected into vaccinia-infected CV-1 cells to assay for transient expression of secreted forms of acidic FGF. (The expected signal cleavage sites of the treated proteins are indicated by heavy arrows in FIG. 15, also deduced according to von Heijne.)

It should be noted that the FGF sequences do not contain traditional signal sequences, and accordingly do not have the capacity to effect their own secretion by the signal hypothesis mechanism under constitutive conditions. It is unclear from the art whether fusing a foreign signal sequence to normal cytoplasmic proteins is capable of effecting their secretion. (It has been shown that β-galactosidase fused to the male signal sequence does not reach the periplasm in bacteria, although Lingappa, V. R., et al, *Proc Natl Acad Sci* (supra) show that β-globin fused to the β-lactamase signal is processed by dog pancreatic microsomes in vitro, and the processed protein is protected from trypsin digestion.)

The ligated signal/FGF-encoding sequences may also be inserted into the MT-II promoter-containing host vectors described above and expressed in CHO cells.

EXAMPLE 11

Bacterial Expression of FGF

The cDNA sequences encoding FGF, which are uninterrupted by introns, are also expressible in bacterial systems. A convenient host vector for expression is pKT52, which contains the "trc" promoter, followed by an ATG start codon. The "trc" promoter contains the upstream portions of the trp promoter and the downstream, operator-containing, regions of the lac promoter. pKT52, containing this promoter was constructed by a simple manipulation of pKK233-2, which is described by Amman, E., et al, *Gene* (1985) 40:183–190: pKK233-2 was digested with EcoRI and PvuII, filled in with dATP and dTTP, and religated to obtain the desired vector.

pKT52 contains in addition to the desired trc promoter and downstream ATG start codon, downstream NcoI, PstI and HindIII sites.

For construction of expression vectors, the FGF-encoding cDNA is obtained by excising with EcoRI or other appropriate enzyme digestion and isolating and, if necessary, modifying the appropriate fragment. The 3' end is prepared for insertion into pKT52 by cutting downstream of the termination codon at any convenient restriction site and supplying PstI or HindIII linkers. The 5' end is prepared by cutting at a site inside the coding sequence and supplying the missing codons and an NcoI site using a synthetic DNA, or by providing an appropriately located NcoI site by mutagenesis. The resulting NcoI/HindIII or NcoI/PstI fragment is then ligated into NcoI/HindIII-digested pKT52 or NcoI/PstI digested pKT52 to provide the FGF-encoding cDNA in reading frame with the ATG start codon. The NcoI/HindIII-bordered Syn-acidic hFGF DNA is inserted directly in this way. Similar vectors are constructed using the human basic FGF encoding DNA.

For bacterial expression, the resulting expression vectors are used to transform *E. coli* MC1061 or other appropriate host cells to $Amp^R$, and the transformed cells are then grown on M9 medium containing 1 mM IPTG for 3–5 hr to an O.D. of 0.2–0.5. (IPTG is a standard inducer for control sequences regulated by the lac operator.) The cells are then harvested, lysed by sonication or treatment with 5% trichloroacetic acid, and the cell extracts assayed for the desired FGF. FGF can be purified from the extracts by methods used for the native protein or by other procedures known in the art.

EXAMPLE 12

Activity of FGF in Promoting Wound Healing

FGF activity in promoting wound healing was assayed using native basic FGF purified from bovine pituitaries by the method of Gospodarowicz et al as a control (*Proc Natl Acad Sci* (USA) (1984) 81:6963–6967). The control bFGF to be assayed was applied to the subcutaneous implantation of polyvinyl alcohol sponges in rats according to the procedure of Davidson, J. M., et al, *J.C.B.* (1985) 100:1219–1227. In the alternative, gortex hollow fibers may also be used (Goodson, W. H., et al, *J Surg Res* (1982) 33:394–401).

In the standard procedure, a total of four rats received two identically treated sponges each. The sponges were either not treated, treated with heparin sepharose beads, treated with FGF bound to heparin sepharose beads using 5 μg FGF per sponge; or treated with 5 μg FGF in solution. The sponges were removed after 6 days and examined histologically for granulation tissue, which is indicative of wound healing.

Sponges which contained FGF showed a higher amount of granulation, which was centered around the heparin sepharose beads in the case of the sponges where the FGF was supplied bound to these beads.

Similar results are observed whether the FGF is from native or recombinant sources and whether the FGF is basic or acidic.

On or before 9 Sep. 1985, Applicant deposited with the American Type Culture Collection (ATCC), Rockville, Md., USA, the λ phage λBA2, λBA3, λHAG-9.1, λBB2, and λKB-7 which were assigned ATCC accession numbers 40195, 40194, 40197, 40196, and 40198, respectively. These deposits were made under conditions as provided under ATCC's agreement for Culture Deposit for Patent Purposes. On or before 12 Sep. 1986, conditions of deposit of λBB2 (ATCC 40196) and λHAG-9.1 (ATCC 40197) were converted to conform to those specified under the Budapest Treaty on the International Recognition of the Deposit of Microorganisms (Budapest Treaty). On or before 12 Sep. 1986, the λ phages designated λHG-3 and λHAG-3 were deposited at ATCC under the terms of the Budapest Treaty and were assigned ATCC accession numbers 40257 and 40258, respectively. Availability of the deposited strains is not to be construed as a license to practice the invention in contravention of the rights granted under the authority of any government in accordance with its patent laws.

We claim:

1. Biologically active recombinant human basic fibroblast growth factor in homogeneous, purified and isolated form, free from any infectious impurities, and free from substances normally accompanying native human basic fibroblast growth factor and from post-translational modifications of the cysteines of native human basic fibroblast growth factor.

2. The recombinant human basic fibroblast growth factor of claim 1 wherein said growth factor has the amino acid sequence numbered 1–146 in FIG. 4.

3. The recombinant human basic fibroblast growth factor of claim 1 wherein said growth factor has the amino acid sequence numbered 16–146 in FIG. 4.

4. The recombinant human basic fibroblast growth factor of claim 1 wherein said growth factor has the amino acid sequence numbered (-9) or (-8) to 146 in FIG. 4.

* * * * *